US006365337B1

(12) United States Patent
Letts et al.

(10) Patent No.: US 6,365,337 B1
(45) Date of Patent: Apr. 2, 2002

(54) GENES ENCODING NEURONAL VOLTAGE-GATED CALCIUM CHANNEL GAMMA SUBUNITS

(75) Inventors: Verity A. Letts; Wayne N. Frankel, both of Bar Harbor, ME (US); Kevin P. Campbell; Ricardo Felix, both of Iowa City, IA (US); Gloria Biddlecome, Coralville, IA (US)

(73) Assignees: University of Iowa Research Foundation, Iowa City, IA (US); The Jackson Laboratory, Bar Harbor, ME (US)

(*) Notice: Subject to any disclaimer, the term of this patent is extended or adjusted under 35 U.S.C. 154(b) by 0 days.

(21) Appl. No.: 09/123,030

(22) Filed: Jul. 27, 1998

(51) Int. Cl.[7] .................. G01N 33/567; C12N 15/00; C07H 21/02
(52) U.S. Cl. ............ 435/1; 536/23.4; 536/23.5; 435/320.1; 435/325; 435/7.21; 435/252.3; 435/7.2
(58) Field of Search .............. 536/23.1, 23.5; 435/69.1, 364, 7.21

(56) References Cited

U.S. PATENT DOCUMENTS

| 5,386,025 A | 1/1995 | Jay et al. ............... 536/23.5 |
| 5,643,750 A | 7/1997 | Spreyer et al. ......... 435/69.1 |
| 5,712,158 A | 1/1998 | Offord ..................... 435/364 |
| 5,726,035 A | 3/1998 | Jay et al. ............... 435/69.1 |

FOREIGN PATENT DOCUMENTS

| WO | WO 95/04144 | * 2/1995 | ............ 536/23.1 |

OTHER PUBLICATIONS

Jay et al., *Science* 248: 490–492 (1990).
Ludwig et al., *J. Neurosci.* 17: 1339–1349 (1997).
Walker and DeWaard, *Trends Neurosci.* 21: 148–154 (1998).
Smart et al., *Neuron* 20: 809–819 (1998).
Homanics et al.., *Proc. Natl. Acad. Sci. USA* 94: 4143–4148 (1997).
Brusa et al., *Science* 270: 1677–1680 (1995).
Fletcher et al., *Cell* 87: 607–617 (1996).
Burgess et al., *Cell* 88: 385–392 1997.
Noebels et al., *Epilepsy Res.* 7: 129–135 (1990).
Sweet et al., *Mouse Genome* 89: 552–553 (1991).
Letts et al., *Genomics* 43:62–68 (1997).
Moon and Friedman, *Genomics* 42: 152–156 (1997).
DeWaard and Campbell, *J. Physiol.* (*Land*) 485: 619–634 (1995).
Ikeda, S.R., *Nature* 380: 255–258 (1996).
Herlitze et al., *Nature* 380: 258–262 (1996).
Pragnell et al., *Nature* 368: 67–70 (1994).
Niidome et al., *Biochem. Biophys. Res. Commun.* 203: 1821–1827 (1994).

* cited by examiner

Primary Examiner—Robert A. Schwartzman
Assistant Examiner—Richard Schnizer
(74) Attorney, Agent, or Firm—Kevin M. Farrell

(57) ABSTRACT

Disclosed are mammalian nucleic acid sequences encoding a neuronal-specific subunit of a voltage-gated calcium channel. Specifically disclosed are $\gamma_2$, $\gamma_3$ and $\gamma_4$ subunits. In other aspects, the disclosure relates to expression vectors which encode neuronal-specific subunits, as well as cells containing such vectors. In other aspects, the disclosure relates to antigenic fusion proteins comprising at least a portion of a mammalian neuronal-specific subunit of a voltage-gated calcium channel. Such fusion proteins are useful, for example, in the production of antibodies specifically reactive with the subunits of the invention. The nucleic acid sequences of the invention find application, for example, in screening for compounds which modulate the activity of neuronal voltage-gated calcium channels and also in diagnostic methods for diagnosing the autoimmune disease Lambert-Eaton Syndrome, as well as diagnosing defects in $\gamma$ subunit genes of a patient with a neuronal disease such as epilepsy. An additional application of the nucleic acid sequences of the invention is in therapeutic methods of treatment for such disorders.

16 Claims, 12 Drawing Sheets cDNA SEQUENCE AND CONCEPTUAL TRANSLATION OF MOUSE Cacng2

```
(-389) gaattcggctgtacoctggcgcgctgtggaagccatctccaaattagcgatcacatatgg
       aaactggagaccagaatttttaggaaaagagattaaggcatctcacttgggggggtggggg
       ggtgttttttatttatttttccctttttttaaaaaaatcgctgcaactggaacagttttt
       gatctcaaaaggcaagcctctcttcccgtgtgatctttataatttacacacttttccgtg
       agctttcttatctccctttttttatatctctccatattctctattcacacatatatcca
       ttataltagtagtggaattaccaatcgcaccctcacacacacgctcctgagaaccagaag
       tcggttgggtgttatataatgaagaatt
```

```
1                                    ATGGGGCTGTTTGATCGAGGTGTTCAAATGC
                                     M  G  L  F  D  R  G  V  Q  M  L
32    TTTTAACCACCGTTGGTGCTTTCGCTGCCTTCAGCTTGATGACCATCGCTGTGGGAACCG
      L  T  T  V  G  A  F  A  A  F  S  L  M  T  I  A  V  G  T  D
92    ACTATTGGCTGTACTCCAGAGGGGTTTGCAAGACCAAAAGTGTCAGTGAGAATGAAACCA
      Y  W  L  Y  S  R  G  V  C  K  T  K  S  V  S  E  N  E  T  S
152   GCAAGAAGAACGAGGAAGTTATGACCCATTCCGGATTATGGAGAACCTGCTGCCTCGAAG
      K  K  N  E  E  V  M  T  H  S  G  L  W  R  T  C  C  L  E  G
212   GGAACTTCAAAGGTCTGTGCAAGCAAATCGACCACTTTCCGGAAGACGCGGACTACGAAG
      N  F  K  G  L  C  K  Q  I  D  H  F  P  E  D  A  D  Y  E  A
272   CTGACACCGCAGAGTATTTCCTCCGGGCCGTGAGGGCCTCGAGTATCTTCCCGATCCTGA
      D  T  A  R  Y  F  L  R  A  V  R  A  S  S  I  F  P  I  L  S
332   GTGTGATCCTGCTTTTCATGGGTGGCCTCTGCATCGCGGCGAGCGAGTTCTACAAGACAC
      V  I  L  L  F  M  G  G  L  C  I  A  A  S  E  F  Y  K  T  R
392   GCCACAACATCATCCTGAGTGCTGGCATCTTCTTCGTGTCTGCAGGTCTTAGTAATATCA
      H  N  I  I  L  S  A  G  I  F  F  V  S  A  G  L  S  N  I  I
452   TCGGGATCATCGTGTATATATCAGCCAATGCTGGAGACCCCTCCAAGAGTGACTCCAAAA
      G  I  I  V  Y  I  S  A  N  A  G  D  P  S  K  S  D  S  K  K
512   AGAACAGCTACTCCTACGGCTGGTCCTTCTACTTCGGGGCCCTGTCCTTCATCATCGCCG
      N  S  Y  S  Y  G  W  S  F  Y  F  G  A  L  S  F  I  I  A  E
572   AGATGGTCGGGGTGCTGGCCGTGCACATGTTTATCGACCGCCACAAACAGCTGCGGGCCA
      M  V  G  V  L  A  V  H  M  F  I  D  R  H  K  Q  L  R  A  T
632   CGGCCCGCGGCCACCGACTACCTCCAGGCCTCCGCCATCACCCGCATCCCCAGCTACCGCT
      A  R  T  D  Y  L  Q  A  S  A  I  T  R  I  P  S  Y  R  Y
692   ACCGCTACCAGCGCCGCAGCCGCTCCAGCTGGCGCTCCACCGAGCCCTCTCACTCCAGAG
      R  Y  Q  R  R  S  R  S  S  G  R  S  T  E  P  S  H  S  R  D
752   ACGCCTCGCCCGTGGGCGTGAAGGGCTTCAACACCCTGCCGTCCACGGAGATCTCCATGT
      A  S  P  V  G  V  K  G  F  N  T  L  P  S  T  E  I  S  M  Y
812   ACACCCTCAGTAGGGACCCCCTGAAGGCTGCCACCACGCCCACCGCCACCTACAACTCGG
      T  L  S  R  D  P  L  K  A  A  T  P  T  A  T  Y  N  S  D
872   ACAGGGATAACAGCTTTCTCCAGGTCCACAACTGTATCCAGAAGGACAGCAAGGACTCTC
      R  D  N  S  F  L  Q  V  H  N  C  I  Q  K  D  S  K  D  S  L
932   TCCACGCCAACACAGCCAACCGCCGGACCACGCCCGTAtgaagaccgtgggacggggac
      H  N  T  A  N  R  R  T  T  P  V
992   cctggggaggcttggccogcgggcgggggagggaccacagcagccacggggagaccttcc
1052  atacgcaaaaaacaacaaacaagcaaacaagcaaacgaacaaacaaacaacaaacaaaca
1112  aaacaaaaacaaaacaaaaaaaagagaaaaacatagcaagtaaattaaaaaaaaaa
```

FIG. 2

```
stg:   1    MGLFDRGVQMLLTTVGAFAAFSLMTIAVGTDYWLYSRGVCKTKSVSENETSKKNEEVMTH   60
            M        T   A  L  +AV TD+W      V      NET       V  H
raty:  1    MSQTKTAKV-RVTLFFILAGGVLAMVAVVTDHW-----AVLSPHLEHHNETC----VAAH   50 stg:  61    SGLWRTCCL------EGNFKGL------CKQIDHF-PEDAD--YEADTAEYFLRAVRA   103
            GLWR C        +N G          C   HF P ++  +E  T +++   A
raty: 51    FGLWRICTTWVAMHNQDKNCSYFRHFNPGESSEIFEFTTQKEYSISAAA           110 stg: 104    SSIFPILSVILLEMGGLCIAASEFYKTRHNIILSAGIFFVSAGLSNIIGILVYISANAGD  163
            +IF   S+  ++G +C A   F   R ++  A +F+ AGL I++ V            +
raty:111    IAIF---SLGFIIGSIC-AFLSFGNKRDYLLRPASMFYAFAGLCLIVSVEVMRQSVKRM  166 stg: 164    PSKSDSKKNSYSYGWSFYFGALSEIIAEMVGVLAVHMFIDRHKQLRATARATDYLQASAI  223
                 D+       Y Y WSF     F + G+ +    + R Q       +
raty:167    IDSEDTVWIEYYYSWSFACACAGETLLFLGGLFLLLFSLPRMPQNPWESCMDTESEH*   223 stg: 224    TRIPSYRYRYQRRSRSSSRSTEPSHSRDASPVGVKGFNTLPSTEISMYTLSRDPLKAATT  283 stg: 284    PTATYNSDRDNSFLQVHNCIQKDSKDSLHANTANRRTTPV*                    323
```

FIG. 3A cDNA SEQUENCE AND CONCEPTUAL TRANSLATION OF MOUSE Cacng3

```
   1   ACTAACTATAGGGCTCGAGCGGCCGCCCGGGCAGGTCACGCGCG
       CACACACGCACACACGCTCACACGCTCACACACCAGACCTCTCTG
       GGTTTCTTTTGCCTTGAGTCTCTCGGGGCTGTGAGAAACCAGGCG
       CATCTCAAACCAAGCTGGCGGCTCCAAGCTCCGAAGCCATGCCCT
       GCACAAACGCTAGTCCTCACCAAGCTCCTGAGGAATGAAAGCAAC
       CCAAGAATCCTCTGACCGCGGCAGTGATGTGGACCAACCCCCTGG
       AGCCCGCACCCTCCCGAGGGCCATAGAGGACTCGGGGAACTGGAG
       AGACCCCAAGACAGGAAATCCCAGCTTTCCCAAAGTCCCCGTGGA
       TGCTGACAAAAGGAGATCTGGATTTTTGGAAGAGGCCGTCCTAGG
       TTACCCAGCTGCAGAGTGATTCTCCCGTCTGTCACTGAATCTACC
       CCTCCAACCCCCAGCCGTTCAGAGTACCATGAAGAATT
 488   atgaggatgtgtgacagaggtatccagatgttgatcactactgta
        M  R  M  C  D  R  G  I  Q  M  L  I  T  T  V
 533   ggagccttcgcagctttagtttaatgaccattgcagtgggcacg
        G  A  F  A  A  F  S  L  M  T  I  A  V  G  T
 578   gactactggctatattccagaggtgtgtgcaggactaaatctaca
        D  Y  W  L  Y  S  R  G  V  C  R  T  K  S  T
 623   agtgacaatgaaaccagcaggaagaatgaagaagtaatgacccac
        S  D  N  E  T  S  R  K  N  E  V  M  T  H
 668   tccgggttgtggaggacctgctgcttggaaggagctttccgaggc
        S  G  L  W  R  T  C  L  E  G  A  F  R  G
 713   gtgtgcaagaaaatcgatcacttcccagaagatgcagactatgaa
        V  C  K  K  I  D  H  F  P  E  D  A  D  Y  E
 758   caggatacagcagaatatcttctacgagctgtgagggcctccagc
        Q  D  T  A  E  Y  L  L  R  A  V  R  A  S  S
 803   gtcttcccatcctcagcgtcactctgctgttttcggggggactc
        V  F  P  I  L  S  V  T  L  L  F  F  G  G  L
 848   tgcgtggctgccagcgagttccaccgcagcaggcacagtgtgatc
        C  V  A  A  S  E  F  H  R  S  R  H  S  V  I
 893   ctcagcgctggcatcttcttcgtctctgcagggctaagcaacatc
        L  S  A  G  I  F  F  V  S  A  G  L  S  N  I
 938   atcggcatcatagtttatatctcagccaatgctggaggccctggg
        I  G  I  I  V  Y  I  S  A  N  A  G  G  P  G
 983   cagagggactctaaaaagagctactcctacggctggtcctttat
        Q  R  D  S  K  K  S  Y  S  Y  G  W  S  F  Y
1028   tttggagccttctctttcatcatcgcggaaattgtgggcgtggtc
        F  G  A  F  S  F  I  I  A  E  I  V  G  V  V
1073   gccgtgcacatctatatcgagaagcatcagcagttgcgtgccaga
        A  V  H  I  Y  I  E  K  H  Q  Q  L  R  A  R
1118   tcccattcagagctcctgaagaagtctacatttgcgcgcctgccg
        S  H  S  E  L  L  K  K  S  T  F  A  R  L  P
1163   ccctacaggtatagattccgaagacggtcaagttctcgctccact
        P  Y  R  Y  R  F  R  R  R  S  S  S  R  S  T
1208   gaacccagatctcgagacctttctcccatcagcaaaggcttccac
        E  P  R  S  R  D  L  S  P  I  S  K  G  F  H
1253   accatcccttccaccgacatctccatgttcaccctctcccgggac
        T  I  P  S  T  D  I  S  M  F  T  L  S  R  D
1298   ccctctaagcttaccatggggacccttctcaactctgaccgggac
        P  S  K  L  T  M  G  T  L  L  N  S  D  R  D
1343   catgcttttctacagttccacaactccacacccaaagagttcaaa
        H  A  F  L  Q  F  H  N  S  T  P  K  E  F  K
1388   gagtcattgcataacaatccggccaacagacgtaccacgcctgtc
        E  S  L  H  N  N  P  A  N  R  R  T  T  P  V
1433   tgaGCTGACCTCTGACCTCTGCCCCGCCGCCCAGCACAGCCTTGG
```

*FIG. 6* cDNA SEQUENCE AND CONCEPTUAL TRANSLATION OF MOUSE Cacng4

```
  22  atggtgcgatgcgaccgcgggctgcagatgctgctgaccacggcc
       M  V  R  C  D  R  G  L  Q  M  L  L  T  T  A
  67  ggagccctcgccgccttctcgctcatggccatcgccatcggcacc
       G  A  L  A  A  F  S  L  M  A  I  A  I  G  T
 112  gactaccggctgtactccagcgcgcacatctgcaacggcaccaac
       D  Y  R  L  Y  S  S  A  H  I  C  N  G  T  N
 157  ctgaccatggacgacgggccccgccccgccgcgctcgcggcgac
       L  T  M  D  D  G  P  P  P  R  R  A  R  G  D
 202  ctcacccattcgggactgtggcgggtgtgttgcatcgaaggcatc
       L  T  H  S  G  L  W  R  V  C  C  I  E  G  I
 247  tatagagggcactgcttccggatcaaccacttcccagaggacaac
       Y  R  G  H  C  F  R  I  N  H  F  P  E  D  N
 292  gattacgaccacgacagctccgagtacctcctccgcattgtgcga
       D  Y  D  H  D  S  S  E  Y  L  L  R  I  V  R
 337  gcctccagtgtctttcccatcctcagcaccattctgctcctgctc
       A  S  V  F  P  I  L  S  T  I  L  L  L  L
 382  ggagggctctgcatcggcgctgggaggatctacagccgcaagaac
       G  G  L  C  I  G  A  G  R  I  Y  S  R  K  N
 427  aatattgtcctcagcgcgggaatcctctttgtggcggcaggcctc
       N  I  V  L  S  A  G  I  L  F  V  A  A  G  L
 472  agtaatatcatcggtatcatcgtctacatttccagcaacacgggc
       S  N  I  I  G  I  I  V  Y  I  S  S  N  T  G
 517  gacccagtgacaaacgtgacgaagacaaaaagaaccattacaac
       D  P  S  D  K  R  D  E  D  K  K  N  H  Y  N
 562  tacggctggtcttttactttggagccctgtcgtttattgtggcg
       Y  G  W  S  F  Y  F  G  A  L  S  F  I  V  A
 607  gagaccgtgggcgtcctggctgtaaacatttacattgagaaaaat
       E  T  V  G  V  L  A  V  N  I  Y  I  E  K  N
 652  aaagagttgaggtttaagaccaagcgggagttccttaaggcctct
       K  E  L  R  F  K  T  K  R  E  F  L  K  A  S
 697  tcctcctctccttacgccaggatgccgagctacaggtaccggcga
       S  S  S  P  Y  A  R  M  P  S  Y  R  Y  R  R
 742  cggcggtccaggtccagttcaaggtccacggaggcctcaccctcc
       R  R  S  R  S  S  S  R  S  T  E  A  S  P  S
 787  agggatgcatctcccgtgggcctgaagatcaccggagccattccc
       R  D  A  S  P  V  G  L  K  I  T  G  A  I  P
 832  atgggtgagctgtccatgtacacgctatccagagaaccccttaag
       M  G  E  L  S  M  Y  T  L  S  R  E  P  L  K
 877  gtgaccacagctgcgagctacagtccggaccaggacgctggcttc
       V  T  T  A  A  S  Y  S  P  D  Q  D  A  G  F
 922  ctgcagatgcatgacttcttccaacaggacctaaaggaaggtttc
       L  Q  M  H  D  F  F  Q  Q  D  L  K  E  G  F
 967  catgtcagcatgctkaaccggcggacractcccgtgTGACCCGCC
       H  V  S  M  L  N  R  R  T  T  P  V
1012  CACCCCTCTCGGCACAGGCCTCCCCCAAGGTGGCTGTTTGTGTGA
      CACACAACAGGGTGA
```

FIG. 7

PROTEIN ALIGNMENTS OF NEURONAL Ca2+ CHANNEL GAMMA SUBUNITS

*FIG. 8A*

```
mCacng2pep 293 ░ N S ░░░ V ░ ░ C I ░░░░ S ░░░░░ T ░░░░░ 322
mCacng3pep 285 ░ H ░ ░░░ F ░ ░ S T P ░ ░ F ░░░░ N ░ P ░░░░░ 314
mCacng4pep 297 ░ A G ░░░ M ░ D F P ░ Q ░ L ░░ G F ░ ░ S M ░░░░░ 326 mCacng2pep 323 ░ 323
mCacng3pep 315 ░ 315
mCacng4pep 327 ░ 327
```

*FIG. 8C*

GENES ENCODING NEURONAL VOLTAGE-GATED CALCIUM CHANNEL GAMMA SUBUNITS

BACKGROUND OF THE INVENTION

Voltage-gated calcium channels are a diverse family of proteins which have a variety of biological functions, including presynaptic neurotransmitter release and protein signaling within the cell (Bito et al. (1997) Curr. Opin. Neurobiol. 7, 419–429; Dunlap et al. (1995) Trends Neurosci. 18, 89–98). The calcium currents produced by these channels are classified into P/Q-, N-, L-, R-, and T-type based on their pharmacological and biophysical properties, and all are expressed in brain (Dunlap et al. (1995) Trends Neurosci. 18, 89–98; Varadi et al. (1995) Trends Pharmacol. Sci. 16, 43–49; Nooney et al. (1997) Trends Pharmacol. Sci. 18, 363–371; Perez-Reyes et al. (1998) Nature 391, 896–900). Except for the T-type, whose molecular structure is unknown, all voltage-gated calcium channels are composed of at least three subunits, $\alpha_1$, $\alpha_2\delta$ and $\beta$ (De Waard et al. Structural and functional diversity of voltage-activated calcium channels. In Ion Channels, (ed. T. Narahashi) 41–87 (Plenum Press, New York, 1996)). A fourth subunit, $\gamma$, is associated with skeletal muscle calcium channels. The mRNA for this $\gamma$ subunit is abundant in skeletal muscle, but has not been detected in brain (Jay, S. D et al. (1990) Science 248, 490–492; Ludwig et al. (1997) J. Neurosci. 17, 1339–1349). Whether $\gamma$ subunits specific for brain calcium channels exist, remains to be determined. The $\alpha_1$ subunit forms the membrane pore and voltage-sensor and is a major determinant for current classification. Several isoforms of $\alpha_1$, arising from different genes, have been identified. The other subunits modulate the voltage-dependence and kinetics of activation and inactivation, and the current amplitude (Walker et al. (1998) Trends Neurosci. 21, 148–154). There is currently only one known gene and isoform for the $\alpha_2\delta$ subunit, and four different $\beta$ subunit genes encoding the distinct $\beta$ isoforms. P/Q- and N-type channels purified from brain contain $\alpha_{1A}$ and $\alpha_{1B}$ subunits, respectively. These $\alpha_1$ subunits are associated with various proportions of the four separately encoded $\beta$ subunit proteins, indicating that considerable subunit complexity exists (Scott et al. (1996) J. Biol. Chem. 271, 3207–3212; Liu et al. (1996) J. Biol. Chem. 271, 13804–13810).

A number of compounds useful in treating various diseases in animals, including humans, are thought to exert their beneficial effects by modulating functions of voltage-gated calcium channels. Many of these compounds bind to calcium channels and block, or reduce the rate of influx of calcium into cells in response to depolarization of the inside and outside of the cells. An understanding of the pharmacology of compounds that interact with calcium channels, and the ability to rationally design compounds that will interact with calcium channels to have desired therapeutic effects, depends upon the understanding of the structure of channel subunits and the genes that encode them. The identification and study of tissue specific subunits allows for the development of therapeutic compounds specific for pathologies of those tissues.

Cellular calcium homeostasis plays an essential part in the physiology of nerve cells. The intracellular calcium concentration is about 0.1 uM compared with 1 mM outside the nerve cell. This steep concentration gradient (×10,000) is regulated primarily by voltage-gated calcium channels. Several pathologies of the central nervous system involve damage to or inappropriate function of voltage-gated calcium channels. In cerebral ischaemia (stroke) the channels of neurons are kept in the open state by prolonged membrane depolarisations, producing a massive influx of calcium ions. This, in turn activates various calcium/calmodulin dependent cellular enzyme systems, e.g. kinases, proteases and phospholipases. Such prolonged activation leads to irreversible damage to nerve cells.

Certain diseases, such as Lambert-Eaton Syndrome, involve autoimmune interactions with calcium channels. The availability of the calcium channel subunits makes possible immunoassays for the diagnosis of such diseases. An understanding of them at the molecular level will lead to effective methods of treatment.

Epilepsies are a heterogeneous group of disorders characterized by recurrent spontaneous seizures affecting 1% of the population. In recent years several human genes have been identified, including the most recently identified potassium channels KCNQ2 and KCNQ3 for benign familial neonatal convulsions (Charlier et al. (1998) Nature Genet. 18, 53–55; Singh et al. (1998) Nature Genet. 18, 25–29; Biervert et al. (1998) Science 279, 403–406). To date, the involvement of voltage-gated calcium channels in epilepsies has been poorly characterized.

A number of mouse mutants have generalized tonic-clonic seizures, mostly resulting from gene knockouts. Ion channels are involved in many of these cases, including potassium (Smart et al. (1998) Neuron 20, 809–819), GABA (Homanics et al. (1997) Proc. Natl. Acad. Sci. USA 94, 4143–4148) and glutamate receptor channels (Brusa, et al. (1995) Science 270, 1677–1680). Comparatively fewer mouse models have been described with absence seizures, (also known as petit-mal or spike-wave), although this may be due to ascertainment bias as these seizures are associated with only a brief loss of consciousness. It has thus required a systematic electrocorticographic screen of known mutants to uncover mouse absence models. The mouse mutants ducky, lethargic, mocha, slow-wave epilepsy, stargazer and tottering, each show some form of spike-wave discharge associated with behavioral arrest which is characteristic of absence epilepsy (Noebels, J. L. In Basic Mechanisms of the Epilepsies: Molecular and Cellular Approaches., (ed. A. V. Delgado-Escueta, A. A. Ward, D. M. Woodbury and R. J. Porter) 44, 97–113 (Raven Press, New York, 1986); Noebels et al. (1990) Epilepsy Res. 7, 129–135; Cox et al. (1997) Cell 91, 1–20). The underlying genes are described in most of these models, and in two—tottering and lethargic—the defect is in a gene encoding a neuronal calcium channel subunit (Fletcher et al. (1996) Cell 87, 607–617; Burgess et al. (1997) Cell 88, 385–392).

Because of the overlap in expression of voltage-gated calcium channel subunits and a limited understanding of tissue differences, it has not been straightforward to study the specific function of neuronal channels in vivo. The study of mouse mutations has begun to allow a dissection of this problem. For example, the neurological mutants tottering and lethargic have defects in genes encoding $\alpha_{1A}$ and $\beta_4$ subunits, respectively (Fletcher et al. (1996) Cell 87, 607–617; Burgess et al. (1997) Cell 88, 385–392). Their phenotypes are very similar, each exhibiting spike-wave seizures and moderate cerebellar ataxia without obvious neuronal damage. The nature of the mutation in each is commensurate with the respective roles of major and auxiliary calcium channel subunits: tottering has an amino acid substitution in the structural $\alpha_{1A}$ subunit, whereas lethargic is not likely to express any functional $\beta_4$ protein. The phenotype of the lethargic mouse shows that defects in regulatory subunits can also lead to the same neuronal malfunctions as observed for structural subunit mutations. Continued study of these mouse mutants will give further insight into neuronal calcium channel function in vivo.

The stargazer mutation arose spontaneously at The Jackson Laboratory on the A/J inbred mouse line (Noebels et al. (1990) Epilepsy Res. 7, 129–135), and was initially detected for its distinctive head-tossing and ataxic gait. Subsequent electrocorticography revealed recurrent spike-wave seizures when the animal was still, characteristic of absence epilepsy. The seizures were notably more prolonged and frequent than in tottering or lethargic mice, lasting on average six seconds and recurring over one hundred times an hour. The ataxia and head-tossing are presumed to be pleiotropic consequences of the mutation in the cerebellum and inner ear, respectively; the latter also distinguishes stargazer from the other mutants. The waggler mutant arose independently on the MRL/MpJ strain and was subsequently found to be an allele of stargazer (Sweet et al. (1991) Mouse Genome 89, 552). Waggler mice are severely ataxic but head-toss less frequently than stargazer and have a more pronounced side-to-side head motion.

The fine-mapping of the stargazer mutation on mouse chromosome 15 and the construction of a 1.3 Mb physical contig across the critical genetic interval was described in an earlier study (Letts et al. (1997) Genomics 43, 62–68). The present invention describes the first member of a multi-gene family that encodes a neuronal specific voltage-gated calcium channel γ subunit disrupted in stargazer and waggler mice.

SUMMARY OF THE INVENTION

In one aspect, the present invention relates to a mammalian nucleic acid sequences encoding a neuronal-specific subunit of a voltage-gated calcium channel. Specifically disclosed are $\gamma_2$, $\gamma_3$ and $\gamma_4$ subunits. In other aspects, the invention relates to expression vectors which encode neuronal-specific subunits, as well as cells containing such vectors. In other aspects, the invention relates to antigenic fusion proteins comprising at least a portion of a mammalian neuronal-specific subunit of a voltage-gated calcium channel. Such fusion proteins are useful, for example, in the production of antibodies specifically reactive with the subunits of the invention. Such antibodies are also encompassed within the scope of the invention.

In another embodiment, the invention relates to a method for screening for compounds which modulate the activity of neuronal voltage-gated calcium channels. The method involves providing a cell transformed with a DNA expression vector comprising a mammalian cDNA sequence encoding a neuronal-specific γ subunit of a voltage-gated calcium channel, the cell comprising additional calcium channel subunits necessary and sufficient for assembly of a functional voltage-gated calcium channel. The cell is contacted with a test compound and agonistic or antagonistic action of the test compound on the reconstituted calcium channels is determined.

Also encompassed within the scope of the invention are diagnostic methods based on the experiments described in the Exemplification section set forth below. These include, for example, a method of diagnosing Lambert-Eaton Syndrome and a method for diagnosing a defect in a γ subunit gene of a patient with a neuronal disease such as epilepsy. Therapeutic methods based on the disclosure are also described.

BRIEF DESCRIPTION OF THE DRAWINGS

FIG. 2 is a diagrammatic representation of the cDNA sequence SEQ ID NO: 7 and conceptual translation of mouse Cacng2 SEQ ID NO: 8.

FIGS. 3A–3B are a diagrammatic representation comparing the $\gamma_2$ subunit protein to the γ subunit of voltage-gated skeletal muscle calcium channels.

FIG. 3a) The predicted open reading frame of cDNA clone c2 SEQ ID NO: 8 is shown on the top line and is aligned with that of the previously identified rat calcium channel γ subunit Genbank accession number CAA70602 on the bottom line. Underlined sequences in each are putative transmembrane regions. The predicted N-glycosylation sites are shown in double underlining, and stippled underlining at the C-terminus indicates the peptide used for antibody generation.

FIG. 3b) Secondary structure prediction plot. Positive scores show residues that are likely to be in the membrane, and negative scores show those that are not.

FIG. 5a) Average whole-cell calcium current in BHK cells. Each bar represents mean ±SE peak calcium current amplitude, and the number of recorded cells is indicated in parentheses.

FIG. 5b) Average normalized current-voltage relationship for control and transfected BHK cells. Symbols represent mean ±SE of six to fourteen cells.

FIG. 5c) Representative superimposed current traces illustrating voltage-dependent inactivation of the channels at steady state from single control and transfected BHK cells. To facilitate comparison of records, currents have been scaled to similar size and only the first 10 ms are displayed.

FIG. 5d) Average steady-state inactivation curves for control and transfected BHK cells.

FIG. 6 is a diagrammatic representation of the cDNA sequence SEQ ID NO:9 and conceptual translation SEQ ID NO: 10 of mouse Cacng3.

FIG. 7 is a diagrammatic representation of the cDNA sequence SEQ ID NO: 11 and conceptual translation SEQ ID NO: 12 of mouse Cacng4.

DETAILED DESCRIPTION OF THE INVENTION

The present invention is based, in one aspect, on the identification of a new mammalian gene encoding a 36 kDa γ subunit of neuronal voltage-gated calcium channels. This gene is referred to herein as Cacng2 and the expressed protein as $\gamma_2$. As detailed in the Exemplification, Cacng2 expression is brain specific and $\gamma_2$ functions in the regulation of voltage-gated calcium channel pores. The predicted protein structure of $\gamma_2$ is similar to that of the γ subunit of skeletal muscle voltage-gated calcium channels, the only γ subunit described prior to the immediate disclosure. Although similar in conserved regions, significant sequence and structural differences exist between γ and $\gamma_2$. For example the $\gamma_2$ subunit is 100 residues longer at its C-terminus as compared to the γ subunit. Data presented in the Exemplification indicates that $\gamma_2$ provides an analogous function in neuronal calcium channels to that of γ in skeletal muscle calcium channels. Cacng2 is the first identified gene in a subsequently identified gene family comprised of at least three different genes encoding neuronal voltage-gated calcium channel γ subunits.

Figure 1:
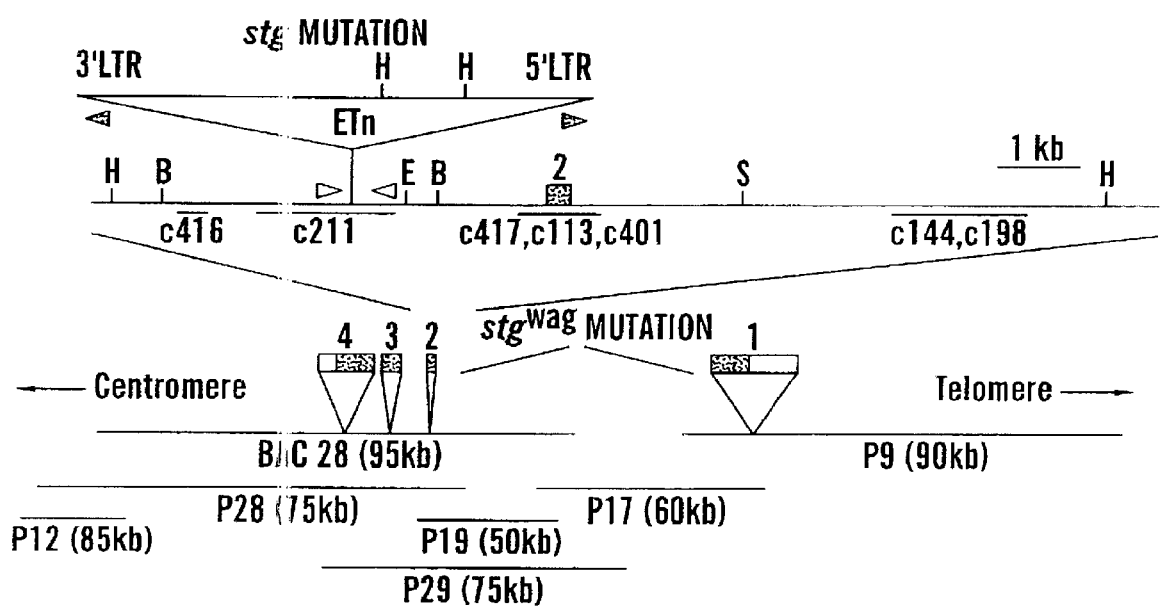
FIG. 1 is a diagrammatic representation which shows the stargazer locus on mouse chromasome 15 and an ETn insertion that is genetically and physically linked to the stg locus. a) Restriction map of the 12 kb HindIII fragment from BAC28, showing the locations of exon 2, cDNA selection products 416, 211, 417, 113, 401, 144, 198 and the ETn insertion. Abbreviations: B, BamHI; E, EcoRI; H, HindIII; S, SacI. Several additional BamHI sites are not shown. The locations of oligonucleotide primers used in genomic DNA PCR reactions are shown here as black arrowheads (left, ETn-OR; right, JS167) and white arrowheads (left, 109F; right, E/Ht7). Below the restriction map are the exons from cDNA clone c2 shown relative to the mouse BAC and PAC contig of Letts et al. (1997) Genomics 43, 62–68. Coding regions are shown in black, untranslated regions in white. Splice site sequences are Exon 1: (donor only) CCTGCT-GCCTCGAAG ' gtatttgatttccaa SEQ ID NO: 1; Exon 2: (acceptor) tgcattatcttgcag ' GGAACTTCAAAGGTC SEQ ID NO: 2, (donor) CAGAGTATTTCCTCC ' gtgagtcaca-cacgg SEQ ID NO: 3; Exon 3: (acceptor) ctctatgttccgcag ' GGGCCGTGAGGGCCT SEQ ID NO: 4, (donor) TCT-TCGTGTCTGCAG ' gtaaggcaggggtgt SEQ ID NO: 5; Exon 4: (acceptor only ) cctcttctcctccag ' GTCTTAGTAATATCA SEQ ID NO: 6.

As detailed in the Exemplification below, murine Cacng2 is encoded by four exons, including an unusually large intron 1. The map position of Cacng2 is diagrammed in FIG. 1. Analysis shows Cacng2 is disrupted in two independent mouse mutants, referred to as stargazer ($Cacng2^{stg}$) and waggler ($cacng2^{wag}$). The Cacng2 allele $Cacng2^{stg}$ is associated with the insertion of an ETn retrotransposon in intron 2 (FIG. 1). Several other mouse mutations have previously been identified as caused by such an insertion (Steinmeyer et al. (1991) Nature 354, 304–308 35; Adachi et al. (1993) Proc. Natl. Acad. Sci. USA 90, 1756–1760 36; Herrmann et al. (1994) Trends in Genet. 10, 280–286 37; Moon et al. (1997) Genomics 42, 152–156). The $Cacng2^{stg}$ mutants have ETn insertions in an intron in the same transcriptional direction as the disrupted gene. This results in premature termination of $Cacng2^{stg}$ transcription, presumably within the element's long terminal repeat (LTR). RNA expression analysis of the $Cacng2^{wag}$ allele shows analogous expression defects mapping to intron 1, implying that the mutation may be due to a similar mechanism. Although the initial identification of Cacng2 is from murine systems, it will be recognized by one of skill in the art that the observations relating to murine Cacng2 and the subsequently identified human Cacng2 described in the Exemplification below, can be applied to the identification of the same gene in other species through the application of merely routine experimentation. In this respect, the methods and compositions of the present invention are applicable to mammalian systems in general.

Another embodiment of the present invention is the murine cDNA sequence encoding a 36 kDa neuronal specific $\gamma_2$ subunit of a voltage-gated calcium channel. Sequences corresponding to both the murine and human cDNAs are listed in FIG. 2 (SEQ ID NO: 7) and disclosed in the Exemplification, respectively, and it will be recognized by one of skill in the art that these sequences can be used for the identification and isolation of the cDNA encoding $\gamma_2$ of other species through the application of routine experimentation.

The cDNA sequence of the present invention can also be characterized as encoding the amino acid sequence shown in FIG. 2, (SEQ ID NO: 8) or equivalents of said amino acid sequence. Equivalents, as used in this context, include peptides of substantially similar length and amino acid identity to those disclosed but having conservative amino acid substitution at a non-critical residue positions. A conservative amino acid substitutions is a substitution in which an amino acid residue is replaced with an amino acid residue of differing identity, but whose R group can be characterized as chemically similar. Four common categories which are defined in standard biochemical texts include: polar but uncharged R groups; positively charged R groups; negatively charged R groups; and hydrophobic R groups. A preferred conservative substitution involves the substitution of a second hydrophobic residue for a first hydrophobic residue, the first and second hydrophobic residues differing primarily in the size of the R group. The hydrophobic residue would be predicted to be located internally in the folded peptide structure and the mild perturbation caused only by a change in the size of an R group at an internal location in the folded peptide structure would not be predicted to alter the antigenic properties of the peptide.

An additional embodiment of the present invention relates to cDNA sequences that are characterized by the ability to hybridize to the nucleic acid sequence shown in FIG. 2, listed in SEQ ID NO: 7, under stringent conditions. A nucleic acid sequence would fall within the scope of the invention, for example, under the following circumstances. The DNA molecule represented in FIG. 2 is fixed to a solid support and a second DNA molecule to be tested for the ability to hybridize to the DNA of FIG. 2 is detectably labeled and suspended in a hybridization buffer consisting essentially of 50% formamide, 5×SSPE (1×SSPE is 0.15 mM NaCl, 1 mM Na-EDTA, 10 mM Na-phosphate (pH 7.0), 5×Denhardt's solution (0.1% polyvinylpyrrolidone, 0.1% Ficoll)). The hybridization buffer is contacted with the solid support at a temperature of about 45° C. for a period of several hours. The hybridization solution is then removed, and non-specifically bound nucleic acid is removed by repeated washing with 1×SSC at increasing temperatures (up to 65° C.).

The isolated cDNA sequence of the present invention can be inserted into an expression vector. Such vectors contain all necessary regulatory signals to promote the expression of a DNA sequence of interest. Expression vectors are typically either prokaryote specific or eukaryote specific. However, vectors have been developed which can be used in either a prokaryotic or eukaryotic system. The use of such vectors is a matter of routine experimentation for one of average skill in the art.

Prokaryotic expression vectors are useful for the preparation of large quantities (e.g., up to milligram quantities) of the protein encoded by the DNA sequence of interest. Eukaryotic expression vectors are useful, for example, when post-translational modification (e.g., glycosylation) of the protein is important. Such post—translational modification can affect the properties of a protein in a variety of ways including the ability of the protein to function in vivo or in vitro; the ability of the protein to form a complex and associate with other proteins or nucleic acids; and the ability of the protein to bind to an antibody or other molecules specific for the protein of interest.

Expression vectors of the types described above can be introduced into either prokaryotic or eukaryotic cells.

Through this technique, cells that express the Cacng2 gene product, either alone or in combination with other calcium channel subunits, can be produced. Such cells can be used to study the biological properties of the protein in an controlled cell system or, alternatively, for the purpose of protein production and purification.

The production of in vitro produced $\gamma_2$ protein can be used for such purposes as biochemical analysis, structural studies, and generation of immunogen. $\gamma_2$ protein can be purified from in vitro systems by a variety of techniques. In one instance, the coding sequence of $\gamma_2$ can be inserted in frame into an expression vector designed to translate the inserted coding sequence as a fusion protein with one member of a specific binding pair. The purification of the fusion protein generated is then achieved by binding to the second member of the specific binding pair which has been fixed to a solid support, with subsequent washing away of any unbound material. Alternatively, more sophisticated purification methods can be used that exploit specific biochemical properties of $\gamma_2$ to separate it from other cellular components. Once antibodies specific for $\gamma_2$ are available immunological purification can also be used.

Following purification by conventional methods, recombinantly produced $\gamma_2$, or an immunogenic portion of same, can be used as a source of highly purified immunogen for the generation of antibodies that specifically bind the $\gamma_2$ protein. Alternatively, a crude lysate can be used in many circumstances.

Polyclonal antibodies can be prepared by immunizing an animal with immunogen prepared as described above using conventional techniques (see e.g., Harlow and Lane (Eds.), *Antibodies, A Laboratory Manual* (Cold Spring Harbor Laboratory, Cold Spring Harbor, N.Y. (1988)). Briefly, the immunized animal is maintained under conditions whereby antibodies reactive with the immunogen are produced. Blood is collected from the animal upon reaching a desired antibody titer. The serum containing the polyclonal antibodies is separated from the other blood components. The polyclonal antibody-containing serum can optionally be further separated into fractions of particular types of antibodies (e.g., IgG or IgM) or monospecific antibodies can be purified from polyclonal antibody containing serum. Similarly, monoclonal antibody secreting hybridomas can be produced using conventional techniques (see e.g., Harlow and Lane (Eds.), *Antibodies, A Laboratory Manual* (Cold Spring Harbor Laboratory, Cold Spring Harbor, N.Y. (1988)).

The Exemplification section which follows describes experiments in which a single immunogenic peptide from the C-terminal portion of $\gamma_2$ was used to immunize animals resulting in the production of antibodies which bind specifically to $\gamma_2$. The peptide corresponds to amino acids 210–323 of the sequence shown in FIG. 2, also listed in SEQ ID NO: 8 and was demonstrated to stimulate an immune response. Thus, in another aspect, the present invention relates to immunogenic peptides capable of stimulating such a response, or equivalents of such peptides.

As mentioned above, another aspect of the current invention relates to eukaryotic cells that have been engineered to express exogenous $\gamma_2$ with other components of voltage-gated calcium channels. These additional subunits comprise isoforms of the $\alpha_1$, $\alpha_2\delta$ and $\beta$ subunits, and any additional molecules that contribute to the function or regulation of the calcium channel, such as G-proteins and G-protein coupled receptors.

Calcium channel $\alpha_1$ pore-forming subunits have been shown to interact with a wide range of cellular factors that modulate the biophysical properties of the channel. One major regulator is G proteins, whose activation reversibly inhibit neuronal non-L type calcium channels. Several classes of G protein-coupled receptors, such as $\alpha$-adrenergic and $\mu$ opiod receptors (Lipscombe et al. (1989) Nature 340, 639–642; Bourinet et al. (1996) Proc. Natl. Acad. Sci. USA 93, 1486–1491), are involved in this regulation. The effects of G proteins on calcium channels are mediated by the G$\beta$/$\gamma$ complex (Ikeda et al. (1996) Nature 380, 255–258; Herlitze et al. (1996) Nature 380, 258–262), by its direct interaction with two major sites in the linker region localized in the intracellular loop connecting the first and second hydrophobic domains (I–II) of the calcium channel $\alpha_1$ subunit (De Waard et al. (1997) Nature 385, 446–450; Zamponi et al. (1997) Nature 385, 442–446). One of these binding sites partially overlaps the site where the calcium channel $\beta$ subunit binds, the $\alpha$-interacting domain (Pragnell et al. (1994) Nature 368, 67–70)). Since the $\beta$ subunit increases calcium channel activity drastically (De Waard et al. (1995) J. Physiol (Lond.) 485, 619–634) this overlap suggests a mechanism for the antagonism between the calcium channel $\beta$ subunit and the G$\beta$/$\gamma$ complex. Further study of calcium channels will likely identify other cellular factors that modulate the activity of calcium channels, either directly or indirectly. The isolation and use of these molecules in the cell systems described above will allow the study of calcium channel subunit interactions as well as direct characterization of fully or partially reconstituted calcium channels under controlled circumstances.

Cell culture systems, such as baby hamster kidney cells (BHK), human embryonic kidney cells (HEK293), and primary oocytes from *Xenopus laevis* are commonly used to reconstitute calcium channels under controlled experimental conditions. Although $\alpha_1$ is sufficient to form an ion pore, the addition of genes expressing regulatory subunits $\beta$ and $\alpha_2\delta$ to these culture systems is critical for the channel to achieve kinetic properties and expression levels like those measured from primary cells (De Waard et al., Structural and functional diversity of voltage-activated calcium channels, In Ion Channels, (ed. T. Narahashi) 41–87 (Plenum Press, New York, 1996)). Specific effects on calcium currents conferred by $\beta$ and $\alpha_2\delta$ subunits in cell culture systems expressing $\alpha_{1A}$, have been described (De Waard et al. (1995) J. Physiol. (Lond) 485, 619–634). The current invention characterizes the effect of incorporating the additional $\gamma_2$ subunit into the system. Additional methods, employing molecular cloning techniques, for the development of a stable cell line for the rapid functional expression of voltage-gated calcium channels have been described previously (Offord et al., U.S. Pat. No. 5,712,158). These techniques are herein incorporated by reference.

The above cell expression systems can be used to study the mechanism of action of the different neuronal calcium channel subunits. The possibility exists that $\gamma_2$ has a unique interaction with a particular channel subunit, such as the recently cloned T-type channel which is apparently not subject to $\beta$ subunit regulation (Perez-Reyes et al. (1998) Nature 391, 896–900; Lambert et al. (1997) J. Neurosci. 17, 6621–6628). It is also possible that while important for channel inactivation, $\gamma_2$ has an additional "downstream" function, for example, direct protein signaling involving its unique cytoplasmic C-terminus, and it is this mechanism that is predominantly involved in the generation of spike-wave seizures.

The present invention provides the first opportunity to use each of the major neuronal calcium channel subunit types together in a recombinant system for testing neuronal calcium channels. Thus the current invention relates to the use of recombinant cell systems described above to develop functional calcium flux assays. Such assays can be used to screen for compounds which modulate the activity, as agonists or antagonists, of neuronal voltage-gated calcium channels. Several examples of such recombinant systems and screening assays have been described (e.g., Spreyer et al. U.S. Pat. No. 5,643,750; Jay et al., U.S. Pat. No. 5,726,035; and Jay et al. U.S. Pat. No. 5,386,025.) The disclosure of these patents are incorporated herein by reference. Potential agonists and antagonists of neuronal voltage-gated calcium channels can be obtained from sources such as pre-existing therapeutic compounds, plant extracts, synthetic chemical libraries, and recombinant molecular libraries. The effectiveness of agonists and antagonists of calcium channels is expected to be of highest physiological relevance when each of the major subunit types $\alpha_{1A}$, $\beta$, $\alpha_2\delta$, and $\gamma$ are present together in a test system. This is due to subunit interactions affecting the accessibility of target sites. As discussed above, additional molecules that contribute to the function or regulation of the neuronal calcium channel can also be included in the recombinant cell system in order to generate calcium channels that more accurately reflect the biological properties of calcium channels in vivo.

As mentioned above, the identification of $\gamma_2$ makes possible studies that provide further insight into $\gamma_2$ function. Such studies can exploit both cell expression systems and Cacng2 mutant mouse systems. The possibilities include defining the $\gamma_2$ subunit's influence on calcium current diversity in neurons, for example, using functional assays with different neuronal $\alpha_1$ genes. Also, experiments relating to the major physical associations between $\gamma_2$ and other subunits, is now possible. The current invention also makes possible the study of neuronal voltage-gated calcium channel function directly in mouse mutants in the most appropriate physiological and genetic contexts. This information will further contribute to the understanding of the native composition and function of voltage-gated calcium channels so that they can be more effectively targeted in the treatment of neurological disorders.

Another aspect of the present invention relates to the method of diagnosing Lambert-Eaton Syndrome. Immunoreactivity towards the $\gamma_2$ protein of a patient suffering symptoms of Lambert-Eaton Syndrome can be determined to specifically diagnose the patient's autoimmune disorder. $\gamma_2$ protein can be obtained by the methods described above. Purified $\gamma_2$ protein can then be combined with antibody-containing serum from the patient to determine if the patient possesses autoimmunity towards $\gamma_2$.

In another aspect, the present invention relates to diagnostic screening techniques useful for the identification of mutations within the Cacng2 gene that are involved in neuronal disorders. Initial identification of mutations responsible for such conditions can be made, for example, by producing cDNA from the mRNA of an individual suffering from a neuronal disorder (e.g., epilepsy). The sequence of nucleotides in the cDNA is then determined by conventional techniques. This determined sequence is then compared to the wild-type sequence disclosed in FIG. 2 (SEQ ID NO: 7). Differences between the determined cDNA sequence, and that disclosed in FIG. 2 are candidate deleterious mutations. Following identification and characterization, oligonucleotides can be designed for the detection of specific mutants. Alternatively, the species of Cacng2 mRNA of a patient can be examined with the technique of semi-quantitative PCR on total mRNA from the patient by sequentially using oligonucleotides specific for the different exons of the Cacng2 gene. Such a method was used in the analysis of Cacng2$^{stg}$ mutant mouse mRNA species detailed in the exemplification.

Alternatively, the Cacng2 gene can be isolated from the genome of a patient and directly examined for mutations by such techniques as restriction mapping or sequencing.

To determine whether such mutations are responsible for the diseased phenotype, experiments can be designed in which the defective gene carrying the identified mutation is introduced into a cell system expressing a complement of components sufficient for the production of functional neuronal voltage-gated calcium channels. The ability of the mutant $\gamma_2$ to function in the calcium channel can be assessed using conventional techniques, such as the ones described above.

Another aspect of the present invention includes the complementation of a defective mutant gene (e.g., identified as described above) in an affected individual by the introduction of a genetic construct carrying DNA encoding functional $\gamma_2$. The introduction of such a complementary copy of the $\gamma_2$ coding sequence can be accomplished through the use of any of the conventional techniques which are known to be effective.

Cacng2 encodes the first identified member of a neuronal voltage-gated calcium channel $\gamma$ subunit family. Other embodiments of the current invention relate to two other known mammalian genes belonging to the neuronal $\gamma$ subunit family, Cacng3 and Cacng4, encoding the $\gamma_3$ and $\gamma_4$ proteins, respectively. $\gamma_3$ and $\gamma_4$ are highly related proteins, and were identified by virtue of their homology to $\gamma_2$. Coding sequences for $\gamma_3$ and $\gamma_4$ are both present in EST databases, indicating that they are expressed proteins. As detailed in the Exemplification, Cacng3 and Cacng4 messages are also brain specific. The high homology to $\gamma_2$ indicates that both proteins have analogous functions to that of $\gamma_2$ with respect to regulating calcium channels. Although similar, the three proteins arise from separate genes that are located at different positions within the genome. The three gene products differ in amino acid sequence and in length. They possibly undergo different post translational modifications and may have subtle or overt differences in function and/or expression, as well as differences in their involvement in neuronal diseases. In light of this, all embodiments of the current invention discussed above for Cacng2 and $\gamma_2$ are also relevant for Cacng3, Cacng4, $\gamma_3$, and $\gamma_4$. The teachings of Cacng2, Cacng3, and Cacng4 enable the identification of other members of the neuronal calcium channel $\gamma$ subunits, and the corresponding cDNAs and proteins encoded through routine experimentation by one of average skill in the art. The nucleic acids can be incorporated in expression vectors and used to express the encoded protein (or portions thereof) for a variety of purposes.

EXEMPLIFICATION

An ETn Insertion Mutation in the Stargazer Critical Interval.

A previously described 1.3 Mb contig of stargazer was comprised of YAC, P1 and BAC recombinant DNA clones (Letts et al. (1997) Genomics 43, 62–68). To identify candidate genes, direct cDNA selection (Morgan et al. (1992) Nucleic Acids Res. 20, 5173–5179) was performed on the two clones, P12 and BAC28, which spanned the stargazer critical interval as defined by genetic recombination. Selection products were screened for expression or structural defects in stargazer mice. By Southern blot hybridization of genomic DNA from mutants and controls, clone c144 identified a 9 kb HindIII restriction fragment in stargazer homozygotes but a 12 kb fragment (BG11) in wild-type A/J mice, the strain on which the stargazer mutation arose. Comparative sequencing showed that six further cDNA selection products were from BG11 (depicted in FIG. 1), including c416. On Southern blots, clone c416 identified a 9 kb BamHI fragment from stargazer, compared to a 3 kb BamHI fragment in A/J (FIG. 1). The hybridization results were consistent with a ~6 kb DNA insertion, containing no BamHI sites but at least one asymmetrically positioned HindIII site. Although several different types of spontaneous proviral insertion mutations have been described in mice, the putative size and restriction map at stargazer was consistent with that of an early transposon (ETn). To test this hypothesis, PCR and sequencing was done using oligonucleotides based on the ETn long terminal repeats (LTR), and flanking genomic DNA from A/J and stargazer mutants including both homozygous and heterozygous genotypes from the B6C3Fe-stg stock and the intersubspecific mapping cross of Letts et al. (1997) Genomics 43, 62–68. Discrete PCR-generated fragments between the LTR primers and the flanking DNA were observed only in stargazer mutants or heterozygotes, but not in wild-type controls, showing that an ETn insertion was uniquely associated with the stargazer mutation.

A Novel Gene Resides at the Stargazer Locus.

Of the cDNA selection products mapping to BG11, only c113 contained a long open reading frame (ORF)—83 bp of which was present in BG11 as a putative exon (FIG. 1). To further explore the coding potential of c113, a mouse brain cDNA library was screened and three clones were sequenced. The longest clone, c2, was over 2.5 kb and included an ORF of 969 bp encoding a putative protein of 323 aa, or 36 kDa. DNA hybridizations and BAC sequencing confirmed that much of c2 originated from BAC28. However, sequences corresponding to more 5' exons, including the first 70 aa of the putative coding region, were not found on BAC 28, but were located on two P1 clones from a more telomeric portion of the contig (FIG. 1). The corresponding 4.5 kb HindIII fragment containing this sequence (including exon 1 and the putative 5' untranslated region) was partly sequenced confirming that the 5' portion of c2 comes from this region. These results are consistent with the stargazer gene having four exons, with intron 1 of 50–90 kb spanning at least two recombinants from the intersubspecific cross. The ETn insertion resides in intron 2 in the same transcriptional orientation as stargazer.

The intron/exon junctions for the mouse stargazer gene were determined from sequence analysis of the mouse cDNA, P1 and BAC (FIG. 1). The sequences match consensus splice sites except for the exon 2 splice donor sequence with a TCC'GT motif, confirmed in multiple independent cDNA and genomic DNA clones. This four exon configuration with a very large first intron is consistent with a partial sequence from the putative human stargazer homologue produced by the Chromosome 22 Sequencing Group at the Sanger Centre; PAC dJ293L6 contains exon 1 and DNA at least 70 kb more centromeric, exons 3 and 4 are present on a neighboring PAC dJ1119A7. The putative translations of human exons 1, 3 and 4 show 98% identity with the corresponding mouse sequence. Presently no epilepsy genes have been mapped to human Chr 22q12-13 but since most epilepsy genes remain unmapped this will be an important locus to check for novel linkages in the future.

Figure 3B:
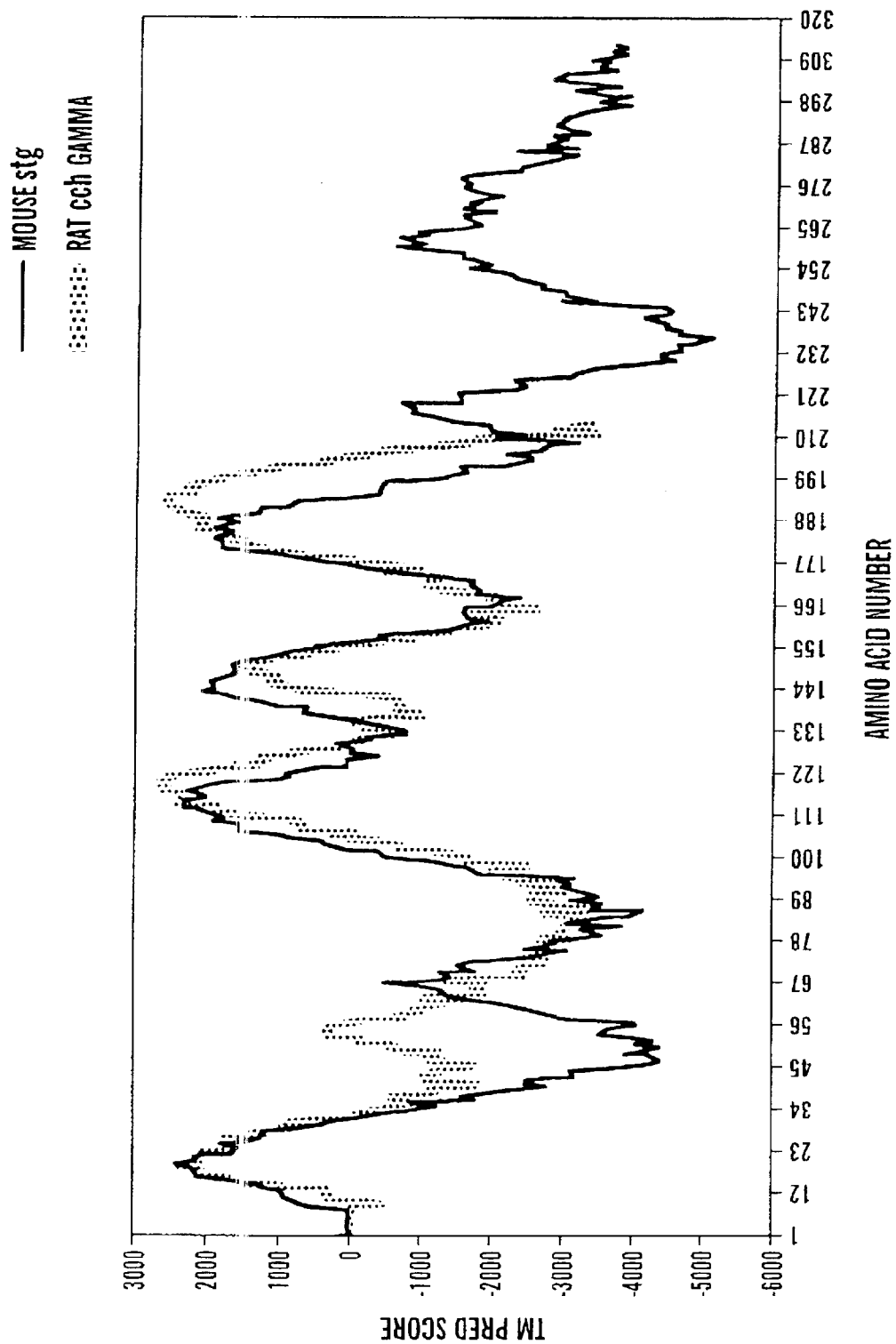

Secondary structure analysis suggests that stargazer encodes a membrane-spanning protein, with a cytosolic N-terminus, four transmembrane domains and a cytosolic C-terminus. Although the stargazer protein was not highly similar to any previously described, a modest partial sequence similarity (25% identity, 38% similarity over 200 amino acids; FIG. 3a) was noted with the γ subunit of the skeletal muscle voltage-gated calcium channel (Jay, S. D et al. (1990) Science 248, 490–492; Eberst et al. (1997) Eur. J. Physiol. 433, 633–637; Wissenbach et al. (1998) Biol. Chem. 379, 45–50), a protein that spans the membrane four times but that is shorter than stargazer by 100 amino acids at the C-terminus. In addition to the strong similarity of the exon structure of the skeletal muscle γ subunit gene to stargazer, the relative location of the putative transmembrane domains, glycosylation site and other predicted properties such as folding and flexibility is also similar to stargazer's secondary structure (FIG. 3).

Stargazer mRNA Expression is Greatly Reduced in Mutant Mice and is Brain-specific.

Figure 4:
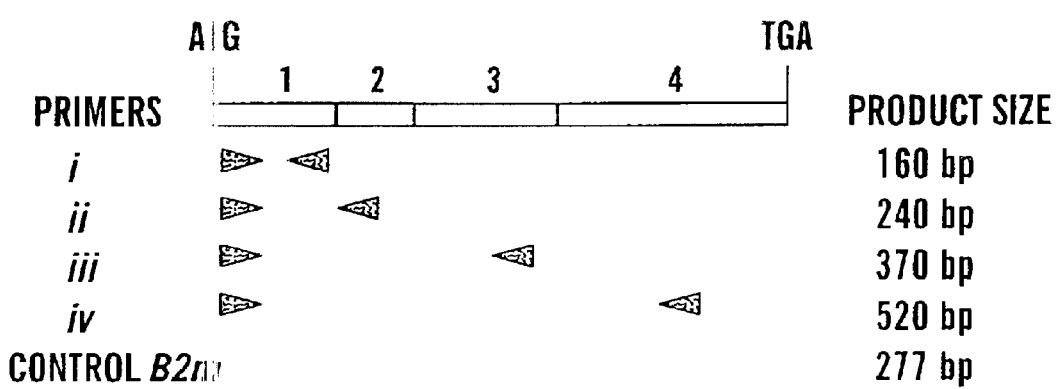
FIG. 4 is a diagrammatic representation of the brain RT-PCR analysis performed, spanning Cacng2 exons in stargazer and waggler mutants. Lanes A, S, M, W and C correspond to A/J, B6C3Fe-stg/stg, MRL/MpJ, B6-stg$^{wag}$/stg$^{wag}$ and no DNA (water) control, respectively, and lane X is the size marker (HaeIII restriction-digested PhiX DNA).

Northern blot analysis was performed on total brain RNA from A/J, B6C3Fe-stg/stg, MRL/MpJ, and B6-stg$^{wag}$/stg$^{wag}$ adult mice, using the c2 cDNA probe, a 1.6 kb EcoRI-XbaI fragment derived from genomic DNA approximately one kb 3' from the end of cDNA clone c2. The analysis revealed a brain-specific RNA of about 6–7 kb, and a smaller, less abundant band of 3 kb, plus several minor species. The smaller transcript was consistent with the c2 cDNA clone, and blot analyses using BAC28—derived probes several kb downstream of the 3' end of c2 showed specific hybridization to this larger 6–7 kb species, suggesting that these messages contained long 3' untranslated regions. Both major species were strikingly absent from stargazer and waggler mutant mice, and were replaced by less abundant, larger species. However, semi-quantitative RT-PCR using oligonucleotide primers from several different regions of the stargazer mRNA showed that both stargazer and waggler mutants produced at least some normally spliced mRNA (FIG. 4), suggesting that neither represents a completely null mutation. The stargazer transcript level is appreciably lower than wild-type downstream of exon 2, suggesting that the ETn insertion causes either premature transcriptional termination or inefficient splicing. Similarly, in the waggler allele transcripts containing exon 1 are detectable at control levels, but those from downstream exons 2, 3 and 4 were much less abundant. Thus, although the waggler mutation is not yet known, by analogy with stargazer it appears to reside in the very large intron 1.

Stargazer mRNA was expressed in adult mouse brain but not in heart, spleen, lung, liver, skeletal muscle, kidney or testis, as determined by RT-PCR and northern blot analysis. A northern blot, containing poly A$^+$ RNA from multiple adult mouse tissues, hybridized to the c2 cDNA probe identified a major transcript of roughly 7.5 Kb, present only in the brain sample. Subsequent probing of the blot with a β-actin probe verified equal loading and transfer of mRNA samples. RT-PCR of total RNA derived from cortex, midbrain, hippocampus, pons, cerebellum and olfactory bulb suggested that stargazer was ubiquitously expressed in the brain. RNA in situ hybridization confirmed this, showing highest expression in cerebellum, olfactory bulb, cerebral cortex, thalamus and CA3 and dentate gyrus regions of the hippocampus.

The Native Stargazer Protein is Enriched on Synaptic Plasma Membranes.

As a first step towards analyzing the stargazer protein in native tissue, a polyclonal antibody against the last 15 amino acids was developed by injection of a KLH-coupled peptide into rabbits. Antibody 239 was used in western blot analysis to probe cell lysates from E. coli transformed with pMal-stg before and after induction, as well as purified MBP-stargazer fusion protein (MBP-stg). Antibody 239 specifically recognized the MBP-stargazer fusion protein present in the induced cell lysates and in the purified preparation. Antibody specificity for stargazer is shown by the detection of only the MBP-stargazer fusion protein in crude *E. coli* cell lysates. Affinity-purified antibody 239 was used as probe in western blot analysis of mouse KCL-washed brain microsomes and synaptic plasma membranes, which revealed that the antibody recognized the native stargazer in brain, determined to be a 38 kDa protein. The presence of excess BSA-coupled antigenic peptide and MBP-stargazer fusion protein completely inhibited binding of antibody 239 to stargazer in brain and synaptic plasma membrane preparations. Immunoprecipitation experiments showed that antibody 239 also recognized the stargazer in vitro translation product, whereas preimmune serum did not. This result verifies that cDNA derived from the c2 clone contains a recognized ORF that is translated into protein.

As expected from the mRNA expression pattern, stargazer protein is present in mouse brain, where the antibody recognized a 38 kDa protein. This band is enriched in mouse synaptic plasma membranes, similar to neuronal calcium channel subunits. As preliminary studies indicate that stargazer is glycosylated, the 38 kDa size is consistent with the predicted translation product plus a N-glycosylation moiety. Interestingly, synaptic plasma membranes also contain a 35 kDa protein not seen in microsomes, even after long ECL exposures, which possibly represents an unglycosylated form. Future studies will clarify the structure and identity of these proteins.

Stargazer Affects Calcium Channel Inactivation Kinetics in Vitro.

Previous studies employing recombinant dihydropyridine (DHP)-sensitive voltage dependent cardiac L-type calcium channels showed that the γ subunit has a pronounced effect on the macroscopic characteristics of the currents transiently expressed in *Xenopus oocytes* or in the mammalian HEK293 cell line. Given the structural similarities between stargazer and the skeletal muscle γ subunit, the possibility that stargazer could modify the biophysical properties of neuronal voltage-dependent calcium channels in a similar manner was investigated. These studies utilized a BHK cell line which stably expresses neuronal $\alpha_1$ class A (P/Q-type) calcium channels ($\alpha_{1A}/\beta_{1a}/\alpha_2/\delta$) (Niidome et al. (1994) Biochem. Biophys. Res. Commun. 203, 1821–1827).

Figure 5A:
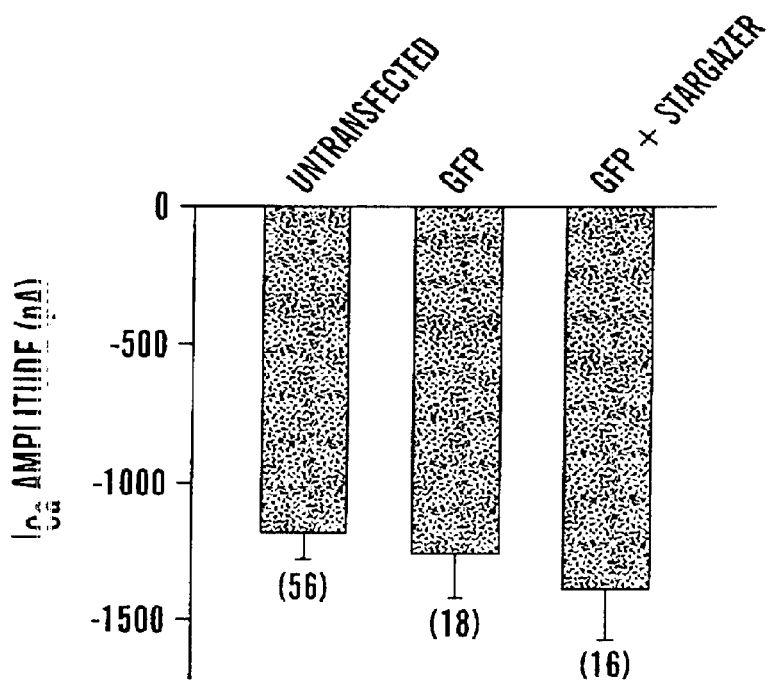
FIGS. 5A–5D is a diagrammatic representation of patch clamp data on the functional effect of the wild-type stargazer protein on neuronal calcium channel activity.
Figure 5B:
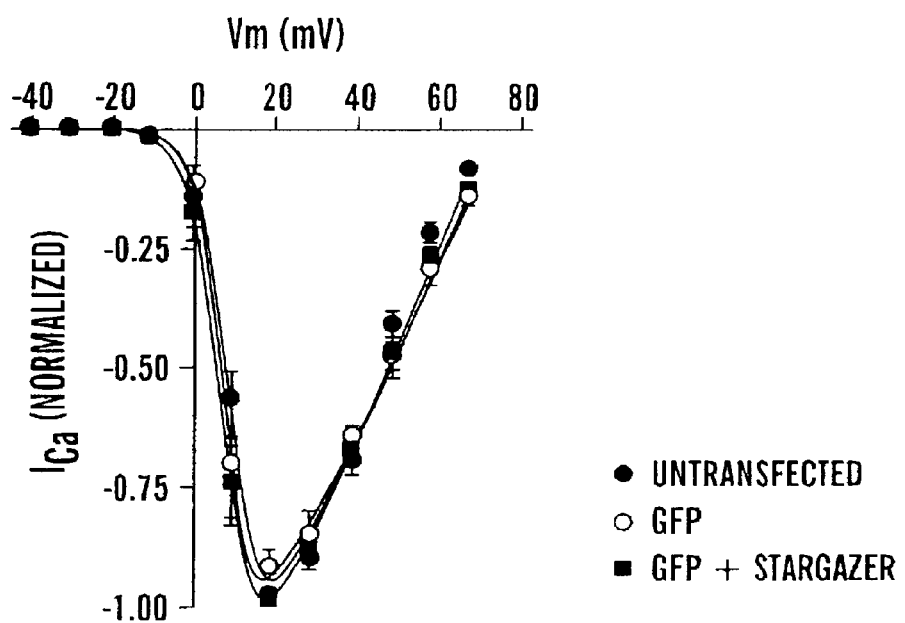

A series of voltage protocols was used to compare the behavior of the channels expressed with and without coexpression of stargazer protein. First, peak calcium current amplitude was examined in response to 40-ms pulses in untransfected and transfected cells at a test potential of +20 mV (FIG. 5a). Although a small difference in current amplitude was observed upon coexpression of stargazer (−1200 (91 pA for control vs. −1401±184 pA for stargazer)), the effect was not statistically significant. Likewise, the properties of the current-voltage relation of the calcium currents were very similar between groups (FIG. 5b).

Figure 5C:
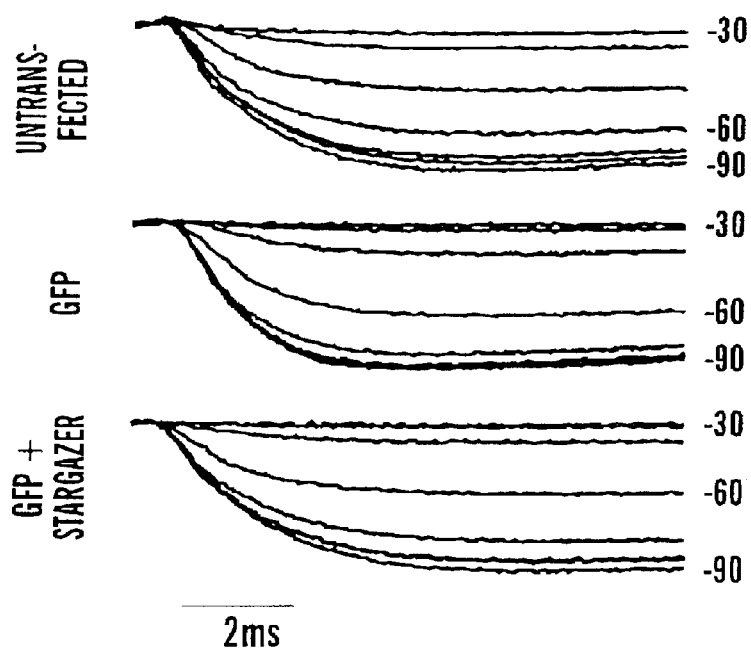
Figure 5D:
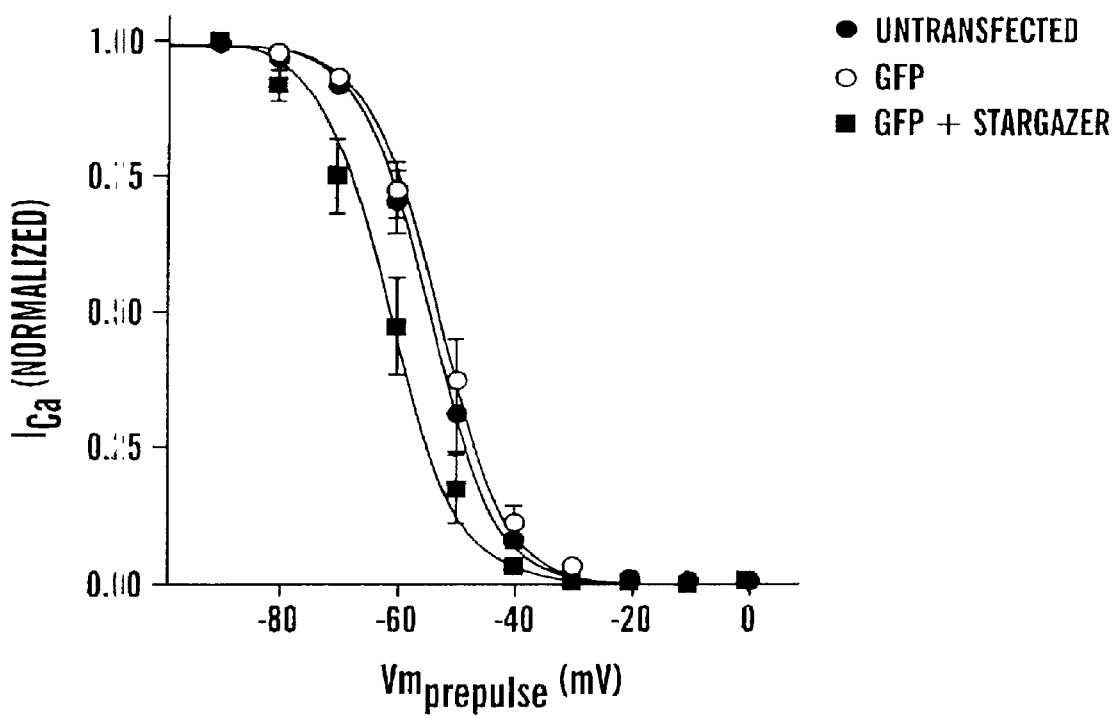

Although coexpression of stargazer protein with neuronal $\alpha_1$ class A calcium channels left the peak current-voltage relationship unchanged, it significantly altered the balance between channel availability and inactivation (FIGS. 5c & 5d). Steady-state inactivation of the calcium channels was measured with and without stargazer using a wide range of 5 s inactivating prepulses. Traces in FIG. 5c show representative records of membrane currents in control and transfected cells at potentials ranging successively from −90 mV through −30 mV prior to a 40-ms step depolarization to a test potential of +20 mV. The results show that current amplitude is decreased as the channels became increasingly inactivated. Notably, the presence of stargazer accentuated this inhibition, shifting the voltage-dependence of channel availability towards more negative potentials. When measurements from individual cells were normalized and averaged, the midpoint voltage ($V_{1/2}$) was higher in cells transfected with stargazer than in control cells, creating a statistically significant ~7 mV hyperpolarizing shift in the voltage-dependence of neuronal $\alpha_1$ class A calcium channel availability in the hypothesized direction (FIG. 5d; p=0.017; one tailed test). These effects cannot be attributed to the mere presence of foreign protein in the plasma membrane of transfected cells, as coexpression of an unrelated protein did not affect $\alpha_1$ class A calcium channel gating.

Identification of Cacng3

Figure 8B:
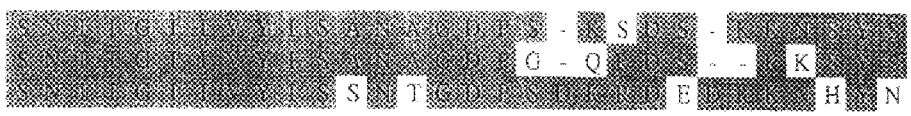
FIG. 8 is a diagrammatic representation of the protein alignments of neuronal calcium channel γ subunits, mCacng2pep SEQ ID NO: 8, mCacng3pep SEQ ID NO: 10, and mCacng4pep SEQ ID NO: 12.

Cacng3 was originally detected in a search of the database of expressed sequence tags (dbEST) of the National Institute for Biotechnology Information (NCBI), for Cacng2 related translation products, using the Basic Local Alignment Search Tool-2 (BLAST 2). This search identified three human brain expressed sequence tags (ESTs) H11833, W29095, and H38324. The corresponding Image Consortium clones were purchased from Research Genetics and sequenced in their entirety. A partial cDNA sequence was obtained from these clones. Oligonucleotide primers were designed and used to amplify a partial cDNA of a mouse homologue by reverse-transcription PCR (RT-PCR) from adult mouse brain total RNA. 5' rapid amplification of cDNA ends (RACE) was performed to obtain missing upstream sequences. This generated several clones containing sequences 5' of the putative start site, based on the Cacng2 gene structure. New oligonucleotides were designed from these products and used in RT-PCR to obtain a complete cDNA clone. The DNA sequence of the cDNA is shown in FIG. 6. A comparison of the predicted amino acid sequence of the translation product to the translation products of the other mouse Cacng genes of the instant invention is shown in FIG. 8.

The entire genomic sequence of a gene that encodes the Cacng3 cDNA sequence was deposited in Genbank (#AC004125) as part of The Institute of Genomic Research (TIGR) effort to sequence human Chromosome 16. The ORF is annotated as "unknown gene product" PID: g3093433. The predicted translation product is highly similar to the mouse homologue. This gene is thought to be the human Cacng3 gene, the human versus mouse sequences have 98% identify and identical lengths. The Cacng3 gene in mouse has been preliminarily mapped to distal mouse Chromosome 7 in a region that has other genes which map to human Chromasome 16p12.

RT-PCR and Northern blot analysis were used to analyze Cacng3 gene expression in different tissues. RT-PCR analysis revealed that Cacng3 mRNA was highly expressed in brain, but was not detected in liver, kidney, lung, heart, spleen, thymus, skeletal muscle or testis. Northern blot analysis was performed on total brain RNA from A/J, B6C3Fe-stg/stg, MRL/MpJ, and B6-stg$^{wag}$/stg$^{wag}$ adult mice, using a Cacng3 probe. This analysis identified a minor transcript of approximately 4 kb, and a major transcript of approximately 2 kb. The minor band was roughly the same size as the major band recognized by a Cacng4 specific probe, described below, and may represent cross-hybridization of the two related species. The Cacng3 probe did not cross-hybridize with the Cacng2 mRNA species identified in the experiments described above, suggesting that the 2 kb band represents the major transcription product of the Cacng3 gene.

Identification of Cacng4

The Cacng4 gene was originally identified in BLAST database searches of the dbEST database for Cacng2 related translation products as mouse embryo EST W85386. The corresponding Image Consortium clone for this EST was purchased from Research Genetics and sequenced in its entirety. 5' RACE was performed using oligonucleotides designed from the sequence, to obtain the 5' end of the cDNA. A second set of oligonucleotides were designed and used in RT-PCR to obtain a complete cDNA. The DNA was sequenced and the data is shown in FIG. 7. A comparison of the predicted amino acid sequence of the predicted translation product to the translation products of the other mouse Cacng genes of the instant invention is shown in FIG. 8.

RNA expression analysis was performed for Cacng4 as described above for Cacng3. This analysis determined that Cacng4 expression is also specific to brain, with a very small amount of material detected in testis. The Cacng4 probe identified a single band of approximately 4 kb with no cross hybridization to any of the other Cacng subunit transcripts previously described. Preliminary mapping efforts place the Cacng4 gene at the middle of mouse Chromosome 11. The human homologue will presumably map to human Chromosome 17 based on extensive conserved syntony between these chromosomes.

Methods

Mice.

The stargazer (stg/stg) and waggler (stg$^{wag}$/stg$^{wag}$) mice arose at The Jackson Laboratory as spontaneous mutations on A/J and MRL/MpJ inbred strains, respectively. Stargazer is now maintained on a hybrid C57BL/6JxC3HeB/FeJ background (B6C3Fe-stg) and waggler on a C57BL/6J background (B6-stg$^{wag}$). All parental, control and mutant stocks are currently maintained at The Jackson Laboratory, where animal procedures were approved by ACUC.

Direct cDNA Selection and Library Screening for Cacng2.

Direct cDNA selection was performed with P1 and BAC clones as described (Morgan et al. (1992) Nucleic Acids Res. 20, 5173–5179) with modifications (Segre et al. (1995) Genomics 28, 549–559). The starting material for the preparation of cDNA selection products was poly(A) mRNA from adult A/J mouse brain. Total RNA was prepared by the Trizol procedure (GIBCO/BRL) and poly(A) mRNA was purified using oligo dT cellulose spin columns (Invitrogen). cDNA selection products had an average length of 500–600 bp. Of 400 cDNA selection products chosen for partial sequencing, about 30% from P12 had high similarity to intracisternal A-type particle proviruses, and about 10% from each clone were similar to moderately repetitive sequences. Twenty cDNA selection products were from an anonymous mouse brain EST mapped to Chr 15 (MDB5079), and a further twenty derived from BAC28 were similar to an EST cluster later identified as the Eif-3a66 gene mapped to human Chr 22 (Unigene ID Hs.55682). In retrospect, many cDNA selection products, including those shown in FIG. 1a, were derived from incompletely spliced mRNA and contained intronic sequences. To find cDNA clones, the Lambda ZAP II ICR outbred mouse brain cDNA library (Stratagene) was screened with the $^{32}$P-labeled cDNA selection product, c113, and phagemids were prepared from the positive plaques following the manufacturer's protocols. All radioactive probes were prepared using the Prime-It kit (Stratagene).

PCR and DNA Sequencing.

Mouse genomic DNA was prepared as described (Taylor et al. (1993) Genomics 16, 380–394). DNA (5 µg/ml) was PCR amplified in a M/J Research PTC-100 machine (1 min 94° C., 2 min 55° C. (62° C. for 3' end primer), 2 min 72° C., for a total of 25–35 cycles). For Cacgn2 experiments, primers were 113F1
(5'-CTCAAAAGCTTGATGACCATC-3'), 113R1
(5'-ACCATCTCGGCGATGATGAAG-3' SEQ ID NO: 14), 113R2
(5'-ACGAAGAAGGTGCCAGCA-3' SEQ ID NO: 15), Exon2OF
(5'-TGCGGTGTCAGCTTCGTAGTC-3' SEQ ID NO: 16), 417-OR
(5'-AAGTTCCCTTCGAGGCAG-3' SEQ ID NO: 17), 109F
(5'-CATTTCCTGTCTCATCCTTTG-3' SEQ ID NO: 18), ETn-OR (3'LTR)
(5'GCCTTGATCAGAGTAACTGTC-3' SEQ ID NO: 19), JS167 (5'LTR) (5'-GAGCAAGCAGGTTTCAGGC-3' SEQ ID NO: 20), and E/Ht7 (5'-ACTGTCACTCTATCTGGAATC-3' SEQ ID NO: 21). Intron regions, including intron/exon boundaries, and 5' and 3' ends were determined by subcloning fragments from P1 and BAC genomic DNA into pGEM1 vector (Promega). Following identification of the correct plasmids by colony hybridization (Sambrook et al. *Molecular Cloning: A laboratory manual 2nd Edition.* (ed. (Cold Spring Harbor Laboratory Press, NY, 1989)), the inserts were subcloned into the pAMP10 vector (GIBCO/BRL) for automated sequencing. All genomic and cDNA clones were sequenced either manually with the Amplicycle Sequencing kit (Perkin Elmer) or with the ABI model 373A automated DNA sequencer (Applied Systems) with M13 primers and the following primers. An overall 3–4 fold coverage of the complete ORF of the cDNA c2 and the 3' genomic region was determined. Internal primers were C2R
(5'-GCGGTTATTGTTCTTGGCGGC-3' SEQ ID NO: 22), C2F
(5'-GGAACTGTGGAACAGGAGTCC-3' SEQ ID NO: 23), 113OF
(5'-TCTGGAGTACAGCCAATA-3' SEQ ID NO: 24), C2F4
(5'-TGGAATTACCAATCGCACC-3' SEQ ID NO: 25), 113OR
(5'-TACGGCTGGTCCTTCTACTTC-3' SEQ ID NO: 26), 113F2
(5'-TAGTAATATCATCGGGAT-3' SEQ ID NO: 27) and 3' end (5'-CCACGGGGAAGACCTTCCATA-3' SEQ ID NO: 28).

Northern Blots and RT-PCR.

Total RNA was prepared from adult mouse brains and 20 µg per lane was run on a 1.2% agarose/formaldehyde gel (Sambrook et al. *Molecular Cloning: A laboratory manual 2nd Edition.* (ed. (Cold Spring Harbor Laboratory Press, NY, 1989)). Following blotting onto Nytran Plus membrane (Schleicher & Schuell), the blot was probed in formamide/hybridization buffer at 42° C. The final wash following hybridization was 0.1×SSC, 0.1% SDS at 65° C. A 1.8 kb mouse actin probe was labeled and used as a control for equal RNA loading. RNA (5 µg) was reverse transcribed with AMV reverse transcriptase (Promega) using the manufacturer's suggested conditions. PCR reactions were run as described above for 25 cycles. Amplifications generating FIG. 4 were performed with the primer pairs i) 113F1, 417-OR, ii) 113F1, Exon2OF, iii) 113F1, 113R2, iv) 113F1, 113R1. The respective amplification products are marked with bullets. The internal standard band migrating near the 0.3 kb marker in each is a 277 bp product generated using primers from the B2m gene, F (5'-CACGCCACCCACCGGAGAATG-3' SEQ ID NO: 29) and R (5'-GATGCTGATCACATGTCTCG-3' SEQ ID NO: 30).

Comparison of γ2 and γ Proteins

The predicted open reading frame of cDNA clone c2 (323 aa) was aligned with that of the rat calcium channel γ subunit (223 aa—EMBL accession # Y09453). The pairwise protein sequence alignment corresponding to Stg amino acids #23-207 was made using Gapped BLAST (Altschul et al. (1997) Nucleic Acids Res. 25, 3389–3402), and the remaining residues were aligned manually. Putative transmembrane regions were predicted by the program TM Pred (Hofmann et al. (1993) Biol. Chem. Hoppe-Seyler 347, 166). Secondary structure prediction plots of $\gamma_2$ and γ were made using TM Pred (Hofmann et al. (1993) Biol. Chem. Hoppe-Seyler 347, 166). Positive scores show residues likely to be in the membrane, and negative scores show those that are not.

RNA in situ Hybridization.

C57BL/6J mice were perfused with 4% paraformaldehyde in phosphate buffered saline (PBS). Brains were collected and immersion fixed for 12 hours in 4% PFA/PBS at 4° C. followed by paraffin embedding. Sections (6 μm) were cleared in xylene, rehydrated in five graded ethanol steps, fixed with 4% PFA fixed for 20 minutes, treated with proteinase K (20 μg/ml) for 7 minutes, refixed for 5 minutes, acetylated in 0.1M triethanolamine/0.25% acetic anhydride for 10 minutes, dehydrated and air dried. The slides were hybridized with probe in 100 μl of hybridization mix (50% formamide, 1×Denhardt's, 10% dextran sulphate, 0.5 μg/ml yeast tRNA, 0.3M NaCl, 5 mM EDTA, 10 mM Tris pH 8.0, 10 mM $NaH_2PO_4$ pH 6.8 and $5\times10^5$ cpm/μl $^{33}P$ labelled probe) for 16 hour at 65° C. in a humid sealed chamber. Sense and antisense cRNA probes were transcribed from a 820 bp EcoR1/Pst1 DNA fragment containing the complete coding region of stargazer with T3 or T7 polymerase (Promega) and [$\alpha^{33}P$]-UTP (NEN). Slides were washed twice in 5×SSC at 55° C., 2×SSC/50% formamide at 65° C. for 30 minutes, rinsed, then RNase A treated for 15 minutes, washed again in 2×SSC/50% formamide at 65° C. for 30 minutes followed by a 2×SSC, 0.5×SSC wash, and finally dehydrated in 5 graded ethanol steps and air dried. Exposures were overnight on Kodak Biomax MR film.

Construction and Purification of Maltose Binding Protein (MBP)-Stargazer Fusion Protein.

nt 658–972 of the c2 clone were amplified by PCR using the forward primer, 5' TCTGAATTCGCCTCCGCCAT-CACCCGCATCCCCAGCTAC SEQ ID NO: 31 and the reverse primer, 5' TATTTCGTCGACTCTTCATACTG-GCGTGGTCCGGCGGTTGG SEQ ID NO: 32. The 350 bp product was ligated into SalI/EcoRI sites of pMal-c2 (New England Biolabs). The accuracy was confirmed by sequencing in both directions.

BL21(DE3) *E. coli*, transformed with pMal-stg, were induced (0.4 mM IPTG) for 3 h, then protease inhibitors (0.1 mM PMSF, 1 mM benzamidine, 10 μg/ml leupeptin and aprotinin, and 2 μg/ml pepstatin A) were added, and the cells were collected by centrifugation at 4000×g for 20 min. The cells were resuspended in 50 ml of buffer 1 (20 mM Tris-Cl, pH 7.4, 200 mM NaCl, 1 mM EDTA, 5 mM DTT, protease inhibitors), subjected to freeze/thaw, sonicated, and centrifuged at 9000×g for 30 min. The supernatant was diluted 3-fold with buffer 1 and rotated with 3 ml amylose resin (New England Biolabs) for 2 h at 4° C. The column was washed with 30 ml buffer 1 and eluted with buffer 1 that contained 10 mM maltose.

Development of Stargazer Antibody.

A synthetic peptide (Research Genetics; CAA plus stargazer sequence DSLHANTANRRTTPV) was coupled to keyhole limpet hemocyanin (KLH) for injection into rabbit 239 (Harlow et al. *Antibodies, A Laboratory Manual.* (ed. 1), (Cold Spring Harbor Laboratory Press, Cold Spring Harbor, 1988)). Serum was affinity-purified (Sharp et al. (1989) J. Biol. Chem. 264, 2816–2825) against MBP-stargazer fusion protein.

Gel Electrophoresis and Western Blotting.

Mouse 2×KCl-washed brain microsomes and synaptic plasma membranes were prepared as described (Jones et al. (1974) Biochim. Biophys. Acta 356, 276–287; Witcher et al. (1994) Meth. Enzymol. 238, 335–348). Reduced, denatured samples were applied to SDS-polyacrylamide gels (Laemmli, U.K.(1970) Nature 227, 680–685). Gels were stained with Gelcode coomassie blue reagent (Pierce) or transferred to Immobilon NC (Millipore) in transfer buffer that contained 20% methanol (40 V, 6 h, 4° C.).

All blotting steps were carried out in 5% non-fat dry milk in PBS, pH 7.4 (Harlow et al. *Antibodies, A Laboratory Manual.* (ed. 1), (Cold Spring Harbor Laboratory Press, Cold Spring Harbor, 1988)). The blot was incubated with primary antibody (1:100) for 12 h at 4° C. and with HRP-conjugated goat anti-rabbit antibody (1:20,000; Boehringer Mannheim) for 1 h at RT. Detection was made with SuperSignal ECL reagent (Pierce) and Kodak X-OMAT film.

Immunoprecipitation of [$^{35}S$]-Met-labeled Stargazer.

Radiolabeled stargazer protein was prepared as instructed in the in vitro coupled transcription/translation rabbit reticulocyte lysate system kit (Promega) using T7 RNA polymerase, 40 μCi of [$^{35}S$]-Met (Amersham; 10 mCi/ml), and 0.6 μg of pcDNA3-stg in in 50 μl reaction volume. Unincorporated [$^{35}S$]-Met was removed by centrifugal gel filtration. Antibody beads were prepared by incubating a 1:1 ratio of either rabbit preimmune serum or antibody 239 with Protein G Sepharose (Pharmacia) overnight at 4° C., followed by 3 washes in PBS. Antibody beads (30 μl) were rotated for four h at 4° C. with 300 μl of [$^{35}S$]-stargazer. Beads were collected by centrifugation, washed three times with column buffer, and bound material eluted with gel loading buffer. Following SDS-PAGE, the gel was washed, dried, and exposed to Kodak BioMax MR film.

Cell culture and transfection.

The cell line BHKBI-6 stably expressing the $\alpha_{1A}$, $\alpha_2\delta$ and $\beta_{1a}$ subunits was established by transfection of baby hamster kidney (BHK) cells with the plasmids pK4KBI ($\alpha_{1A}$), pCAA2 ($\alpha_2\delta$) and pCABE ($\beta_{1a}$) and selection in Dulbecco's modified Eagle's medium (DMEM) containing G418 and methotrexate (Niidome et al. (1994) Biochem. Biophys. Res. Commun. 203, 1821–1827). For use, the cells were grown in DMEM supplemented with 5% fetal bovine serum, 30 U/ml penicillin, 30 μg/ml streptomycin, 250 μM methotrexate and 600 μg/ml G418 at 37° C. in a 5% $CO_2$ humidified atmosphere. Cells were fed every other day and subcultured once weekly up to passage eight. Transient transfections were performed using the calcium-phosphate method (Kingston, R. E. Introduction of DNA into mammalian cells. *In Current Protocols in Molecular Biology*, (ed. F. M. Ausubel, R. Brent, R. E. Kingston, D. D. Moore, J. G. Seidman, J. A. Smith and K. Struhl) 9.1.1–9.1.11 (John Wiley & Sons, New York, 1997)) with 3 μg plasmid cDNA encoding the mouse stargazer protein. The construct was made by assembling a HindIII/KpnI 1.5 kb fragment of the stargazer c2 clone containing the entire ORF into the pcDNA3 expression vector (Invitrogen). To select positively transfected cells for electrophysiology, a plasmid encoding the green fluorescent protein (pGreen Lantern-1; GIBCO/BRL) was added to the DNA transfection mixture (1:1).

Current Recordings.

Calcium channel currents were recorded from BHK cells according to the whole-cell patch-clamp technique (Hamill et al. (1981) Eur. J. Physiol. 391, 85–100). All recordings were performed at room temperature using an Axopatch 200A patch-clamp amplifier (Axon Instruments) and 2–4 MΩ micropipettes manufactured from borosilicate glass capillary tubes. Cells were clamped at a holding potential of −90 mV and capacity transients were electronically compensated. Currents were evoked by 40-ms depolarizing voltage steps (0.05 Hz) to test potentials ranging from −40 to +70 mV. To measure calcium channel inactivation at steady-state, cells were held for 5 s at potentials ranging successively from −90 through 0 mV prior to a 40-ms step depolarization to a test potential of +20 mV. Linear leak and residual capacity currents were subtracted on-line using a P/4 standard protocol. Current records were captured on-line and digitized at a sampling rate of 20 kHz following filtering of the current record (5 kHz; 4-pole Bessel filter) using a personal computer attached to a TL-1 interface (Axon). Pulse protocols, data capture and analysis of recordings were performed using pCLAMP software (Axon). To isolate calcium currents, cells were bathed in a solution containing (in mM): $CaCl_2$ 10; tetraethylammonium chloride (TEA-Cl) 125; HEPES 10; glucose 5. The bath solution was adjusted to pH 7.3 with TEA-OH and to 300 mosml $l^{-1}$ with sucrose. The internal (patch pipette) solution consisted of (mM): CsCl 135; $MgCl_2$ 5; EGTA 10; HEPES 10; ATP (magnesium salt) 4; GTP 0.1 (pH 7.3/CsOH, 286 mosml $l^{-1}$). The statistical significance of differences in mean current amplitude and $V_{1/2}$ between cells expressing stargazer and control was determined by one-way ANOVA, followed by Duncan's new multiple range test.

Currents were elicited by 40-ms pulses from a holding potential of −90 mV to a test potential of +20 mV in untransfected and transiently transfected cells expressing GFP alone or in combination with 2 Cells were held at −90 mV, and 40-ms command steps to the indicated voltages (Vm) were given sequentially at 20-s intervals. Peak currents measured at each command step were normalized to the maximum current observed in each cell, averaged and plotted as a function of voltage. Smooth curves are Boltzmann functions of the type $I^{Ca}=[g(TP-E)]/[1+\exp(-(TP-V_{1/2})/s)]$, where g is the maximum normalized conductance; E, the reversal potential; $V_{1/2}$, the potential of half activation; and s, the range of potential for an e-fold change around $V_{1/2}$. For the fitted control curve g=0.02; E=76 mV; $V_{1/2}$=−10 mV; and s=4.1 mV. For the curve in cells transiently expressing GFP alone g=0.02; E=78 mV; $V_{1/2}$=−8 mV; and s=3.7 mV; and for the curve in cells co-expressing GFP and the stargazer protein g=0.02; E=78 mV; $V_{1/2}$=−8 mV; and s=4.1 mV. Symbols represent mean ±SE of six to fourteen cells. Representative superimposed current traces illustrating voltage-dependent inactivation of the channels at steady state from single control and transfected BHK cells shown in FIG. 5c were generated as follows. Individual currents in each cell were evoked by a 40-ms duration voltage step to +20 mV from a 5 s inactivating prepulse (ranging the voltages shown at the right) prior to the test potential. To facilitate comparison of records, currents have been scaled to similar size and only the first 10 ms are displayed. Average steady-state inactivation curves for control and transfected BHK cells shown in FIG. 5d were done as follows. Currents were obtained as in c). Values were expressed as a fraction of the maximum amplitude seen in each cell, averaged and plotted as a function of voltage. Curves were fitted with a single Boltzmann equation of the form $I_{Ca}=1/[1+\exp((TP-V_{1/2})/s)]$, where $V_{1/2}$, is the voltage for 50% inactivation and s, the slope factor. For control cells $V_{1/2}$=−54.7±1.6 mV and s=5.6±0.5 mV; for cells expressing GFP, $V_{1/2}$=−53.4±1.9 mV and s=5.7±0.2 mV; and for cells expressing GFP and stargazer protein $V_{1/2}$=−61.0±2.8 mV and s=5.8±0.2 mV. Symbols represent pooled data from six to seven cells.

Cacng3 and Cacng4 Sequencing.

DNA sequencing was done as described above using either standard M13F or M13R vector sequencing primers, or using primers described below.

Cacng3 and Cacng4 Northern Blots, RT-PCR and 5' RACE

Northern blot and RT-PCR procedures were done as described above with the exception of the gene-specific oligonucleotides and hybridization probes. Some of the hybridization probes were obtained from rough sequence, not reported here, that was reliable enough in the regions from which the oligonucleotides were designed. The oligonucleotides used to amplify mouse Cacng3 from total adult mouse brain RNA were based on the sequence of the putative corresponding human ESTs: HSLF1-5'TGTGGAGGACCTGCTGCCTAGAAG 3' SEQ ID NO: 33, HSLR1-5' ACCATCACAAGGACCATGCCATGC 3' SEQ ID NO: 34, and HSLR 2-5' CAGAGACATCTCTG-TACACTTCCC 3' SEQ ID NO: 35. HSLR1 and HSLR2 were used for 5' RACE (Frohman et al. (1993) Methods Enzymol 218, 340–356) using mouse brain Marathon cDNA from Clontech (Clontech, Inc), which was done as described by the manufacturer with the modification of using Boehringer Expand/Taq polymerase (Boehringer-Mannheim, Inc). RACE products were subcloned and sequenced into the pCR2 vector using the TA cloning kit (Invitrogen) as described above. The Cacng3 oligonucleotide primers used in the RT-PCR were HDLF5-5' GCAAAGGCTTCCACAC-CATC 3' SEQ ID NO: 36, AND HSLR1. The B2m control oligonucleotides for RT-PCR were as described above for Cagng2. The probe used on the northern blot was an 800 bp fragment generated from mouse cDNA using primers HSLF1 and HSLR2. To obtain sequences 5' of the putative start codon of Cacng4, 5' RACE, subcloning and sequencing was done as above, with Cacng4-specific oligonucleotides W85386-R1-5' GGAAGGACAGAGTCAAAGGC 3' SEQ ID NO: 37 and W85386-R3-5' AAGAGGCCTTAAG-GAACTCC 3' SEQ ID NO: 38 based on our sequence of the mouse EST W85386. The Cacng4 oligonucleotide primers used in the RT-PCR were W85386-F2 5' CTGAGCTCA-GAATGTACAGG 3' SEQ ID NO: 39 and W85386-R2-5' ATCTGTGTCAGAACACCAGG 3'SEQ ID NO: 40. The B2m control oligonucleotides were as described above for Cacng2. The Cacng4 probe used on the northern blot was the W85386 EST itself.

Nomenclature, Accession Numbers.

Consistent with calcium channel and mouse genetic nomenclature, we propose that the mouse gene symbol for stargazer be changed to Cacng2 and the stargazer and waggler alleles $Cacng2^{stg}$ and $Cacng2^{stg\text{-}wag}$, respectively.

What is claimed is:

1. An isolated nucleic acid which encodes a $\gamma_2$ subunit of a voltage-gated calcium channel with the amino acid sequence of SEQ ID NO: 8.

2. The isolated nucleic acid of claim 1 which is nucleotide 390-1358 of SEQ ID NO: 7.

3. An isolated genomic DNA encoding a $\gamma_2$ subunit of a voltage-gated calcium channel with the amino acid sequence of SEQ ID NO: 8.

4. A DNA expression vector comprising a nucleic acid sequence which encodes a $\gamma_2$ subunit of a voltage-gated calcium channel with the amino acid sequence of SEQ ID NO: 8.

5. The DNA expression vector of claim 4 wherein the nucleic acid sequence is nucleotide 390-1358 of SEQ ID NO: 7.

6. A cell transformed with a DNA expression vector comprising a nucleic acid sequence which encodes a $\gamma_2$ subunit of a voltage-gated calcium channel with the amino acid sequence of SEQ ID NO: 8.

7. The cell of claim 6 wherein the nucleic acid sequence is SEQ ID NO: 7.

8. The cell of claim 6 which is prokaryotic.

9. The cell of claim 6 which is eukaryotic.

10. The cell of claim 6 which is also transformed with DNA expression vectors encoding additional calcium channel subunits necessary and sufficient for assembly of a functional voltage-gated calcium channel.

11. A recombinant DNA expression vector comprising a nucleic acid sequence which encodes an antigenic fusion-protein comprising a C-terminal portion of a $\gamma_2$ subunit of a voltage-gated calcium channel with the amino acid sequence of SEQ ID NO: 8.

12. A cell transformed with a recombinant DNA expression vector comprising a nucleic acid sequence which encodes an antigenic fusion protein comprising a C-terminal portion of a $\gamma_2$ subunit of a voltage-gated calcium channel with the amino acid sequence of SEQ ID NO: 8.

13. An isolated cDNA which encodes a $\gamma_2$ subunit of a voltage-gated calcium channel with the amino acid sequence of SEQ ID NO: 8.

14. An isolated nucleic acid comprising SEQ ID NO: 7.

15. The recombinant DNA expression vector of claim 11 wherein the C-terminal portion of the $\gamma_2$ subunit encoded by the nucleic acid is amino acid 210-323 of SEQ ID NO: 8.

16. A method for identifying candidate compounds for modulating the activity of human neuronal voltage-gated calcium channels, comprising:

a) providing a cell culture model system comprising cells transformed with a DNA expression vector comprising a nucleic acid sequence which encodes a $\gamma_2$ subunit of a voltage-gated calcium channel with the amino acid sequence of SEQ ID NO: 8, said cell comprising additional calcium channel subunits necessary and sufficient for assembly of a functional voltage-gated calcium channel;

b) contacting the cell culture model system of step a) with a test compound; and c) measuring calcium channel currents in at least one cell of the cell culture model system, wherein an increase or decrease in the calcium channel currents in the presence of the test compound, compared to calcium channel currents measured in the absence of the test compound, identifies the test compound as a candidate compound for modulating the activity of human neuronal voltage-gated calcium channels.

* * * * *

SEQUENCE LISTING

<160> NUMBER OF SEQ ID NOS: 40

<210> SEQ ID NO 1
<211> LENGTH: 30
<212> TYPE: DNA
<213> ORGANISM: Murinae gen. sp.

<400> SEQUENCE: 1
cctgctgcct cgaaggtatt tgatttccaa                                      30

<210> SEQ ID NO 2
<211> LENGTH: 30
<212> TYPE: DNA
<213> ORGANISM: Murinae gen. sp.

<400> SEQUENCE: 2
tgcattatct tgcagggaac ttcaaaggtc                                      30

<210> SEQ ID NO 3
<211> LENGTH: 30
<212> TYPE: DNA
<213> ORGANISM: Murinae gen. sp.

<400> SEQUENCE: 3
cagagtattt cctccgtgag tcacacacgg                                      30

<210> SEQ ID NO 4
<211> LENGTH: 30
<212> TYPE: DNA
<213> ORGANISM: Murinae gen. sp.

<400> SEQUENCE: 4
ctctatgttc cgcaggggcc gtgagggcct                                      30

<210> SEQ ID NO 5
<211> LENGTH: 30
<212> TYPE: DNA
<213> ORGANISM: Murinae gen. sp.

<400> SEQUENCE: 5
tcttcgtgtc tgcaggtaag gcagggtgt                                       30

<210> SEQ ID NO 6
<211> LENGTH: 30
<212> TYPE: DNA
<213> ORGANISM: Murinae gen. sp.

<400> SEQUENCE: 6
cctcttctcc tccaggtctt agtaatatca                                      30

<210> SEQ ID NO 7
<211> LENGTH: 1558
<212> TYPE: DNA
<213> ORGANISM: Murinae gen. sp.
<220> FEATURE:
<221> NAME/KEY: 5'UTR
<222> LOCATION: (1)..(389)
<220> FEATURE:
<221> NAME/KEY: CDS
<222> LOCATION: (390)..(1361)
<220> FEATURE:
<220> FEATURE:
<221> NAME/KEY: 3'UTR
<222> LOCATION: (1361)..(1558)

<400> SEQUENCE: 7

```
gaattcggct gtaccctggc gcgctgtgga agccatctcc aaattagcga tcacatatgg        60
aaactggaga ccagaatttt aggaaaagag attaaggcat ctcacttggg ggggtggggg       120 ggtgttttt atttattttc ccttttttta aaaaaatcgc tgcaactgga acagtttttt        180
gatctcaaaa ggcaagcctc tcttcccgtg tgatctttat aatttacaca cttttccgtg       240
agctttctta tctccctttt ttttatatct ctccatattc tctattcaca catatatcca       300
ttatattagt agtggaatta ccaatcgcac cctcacacac acgctcctga gaaccagaag       360
tcggttgggt gtttatataa tgaagaatt atg ggg ctg ttt gat cga ggt gtt        413
                                 Met Gly Leu Phe Asp Arg Gly Val
                                  1               5
```

| | | | | | | | | | | | | | | | |
|---|---|---|---|---|---|---|---|---|---|---|---|---|---|---|---|
| caa | atg | ctt | tta | acc | acc | gtt | ggt | gct | ttc | gct | gcc | ttc | agc | ttg | atg | 461 |
| Gln | Met | Leu | Leu | Thr | Thr | Val | Gly | Ala | Phe | Ala | Ala | Phe | Ser | Leu | Met |
| | 10 | | | | 15 | | | | | 20 | | | | | |
| acc | atc | gct | gtg | gga | acc | gac | tat | tgg | ctg | tac | tcc | aga | ggg | gtt | tgc | 509 |
| Thr | Ile | Ala | Val | Gly | Thr | Asp | Tyr | Trp | Leu | Tyr | Ser | Arg | Gly | Val | Cys |
| 25 | | | | | 30 | | | | | 35 | | | | | 40 |
| aag | acc | aaa | agt | gtc | agt | gag | aat | gaa | acc | agc | aag | aag | aac | gag | gaa | 557 |
| Lys | Thr | Lys | Ser | Val | Ser | Glu | Asn | Glu | Thr | Ser | Lys | Lys | Asn | Glu | Glu |
| | | | | 45 | | | | | 50 | | | | | 55 | |
| gtt | atg | acc | cat | tcc | gga | tta | tgg | aga | acc | tgc | tgc | ctc | gaa | ggg | aac | 605 |
| Val | Met | Thr | His | Ser | Gly | Leu | Trp | Arg | Thr | Cys | Cys | Leu | Glu | Gly | Asn |
| | | | 60 | | | | | 65 | | | | | 70 | | |
| ttc | aaa | ggt | ctg | tgc | aag | caa | atc | gac | cac | ttt | ccg | gaa | gac | gcg | gac | 653 |
| Phe | Lys | Gly | Leu | Cys | Lys | Gln | Ile | Asp | His | Phe | Pro | Glu | Asp | Ala | Asp |
| | | 75 | | | | | 80 | | | | | 85 | | | |
| tac | gaa | gct | gac | acc | gca | gag | tat | ttc | ctc | cgg | gcc | gtg | agg | gcc | tcg | 701 |
| Tyr | Glu | Ala | Asp | Thr | Ala | Glu | Tyr | Phe | Leu | Arg | Ala | Val | Arg | Ala | Ser |
| | 90 | | | | | 95 | | | | | 100 | | | | |
| agt | atc | ttc | ccg | atc | ctg | agt | gtg | atc | ctg | ctt | ttc | atg | ggt | ggc | ctc | 749 |
| Ser | Ile | Phe | Pro | Ile | Leu | Ser | Val | Ile | Leu | Leu | Phe | Met | Gly | Gly | Leu |
| 105 | | | | | 110 | | | | | 115 | | | | | 120 |
| tgc | atc | gcg | gcg | agc | gag | ttc | tac | aag | aca | cgc | cac | aac | atc | atc | ctg | 797 |
| Cys | Ile | Ala | Ala | Ser | Glu | Phe | Tyr | Lys | Thr | Arg | His | Asn | Ile | Ile | Leu |
| | | | | 125 | | | | | 130 | | | | | 135 | |
| agt | gct | ggc | atc | ttc | ttc | gtg | tct | gca | ggt | ctt | agt | aat | atc | atc | ggg | 845 |
| Ser | Ala | Gly | Ile | Phe | Phe | Val | Ser | Ala | Gly | Leu | Ser | Asn | Ile | Ile | Gly |
| | | | 140 | | | | | 145 | | | | | 150 | | |
| atc | atc | gtg | tat | ata | tca | gcc | aat | gct | gga | gac | ccc | tcc | aag | agt | gac | 893 |
| Ile | Ile | Val | Tyr | Ile | Ser | Ala | Asn | Ala | Gly | Asp | Pro | Ser | Lys | Ser | Asp |
| | | 155 | | | | | 160 | | | | | 165 | | | |
| tcc | aaa | aag | aac | agc | tac | tcc | tac | ggc | tgg | tcc | ttc | tac | ttc | ggg | gcc | 941 |
| Ser | Lys | Lys | Asn | Ser | Tyr | Ser | Tyr | Gly | Trp | Ser | Phe | Tyr | Phe | Gly | Ala |
| | 170 | | | | | 175 | | | | | 180 | | | | |
| ctg | tcc | ttc | atc | atc | gcc | gag | atg | gtc | ggg | gtg | ctg | gcc | gtg | cac | atg | 989 |
| Leu | Ser | Phe | Ile | Ile | Ala | Glu | Met | Val | Gly | Val | Leu | Ala | Val | His | Met |
| 185 | | | | | 190 | | | | | 195 | | | | | 200 |
| ttt | atc | gac | cgc | cac | aaa | cag | ctg | cgg | gcc | acg | gcc | cgc | gcc | acc | gac | 1037 |
| Phe | Ile | Asp | Arg | His | Lys | Gln | Leu | Arg | Ala | Thr | Ala | Arg | Ala | Thr | Asp |
| | | | | 205 | | | | | 210 | | | | | 215 | |
| tac | ctc | cag | gcc | tcc | gcc | atc | acc | cgc | atc | ccc | agc | tac | cgc | tac | cgc | 1085 |
| Tyr | Leu | Gln | Ala | Ser | Ala | Ile | Thr | Arg | Ile | Pro | Ser | Tyr | Arg | Tyr | Arg |
| | | | 220 | | | | | 225 | | | | | 230 | | |
| tac | cag | cgc | cgc | agc | cgc | tcc | agc | tcg | cgc | tcc | acc | gag | ccc | tct | cac | 1133 |
| Tyr | Gln | Arg | Arg | Ser | Arg | Ser | Ser | Arg | Ser | Thr | Glu | Pro | Ser | His |
| | | 235 | | | | | 240 | | | | | 245 | | | |

```
tcc aga gac gcc tcg ccc gtg ggc gtg aag ggc ttc aac acc ctg ccg   1181
Ser Arg Asp Ala Ser Pro Val Gly Val Lys Gly Phe Asn Thr Leu Pro
    250                 255                 260 tcc acg gag atc tcc atg tac acc ctc agt agg gac ccc ctg aag gct   1229
Ser Thr Glu Ile Ser Met Tyr Thr Leu Ser Arg Asp Pro Leu Lys Ala
265                 270                 275                 280 gcc acc acg ccc acc gcc acc tac aac tcg gac agg gat aac agc ttt   1277
Ala Thr Thr Pro Thr Ala Thr Tyr Asn Ser Asp Arg Asp Asn Ser Phe
                285                 290                 295 ctc cag gtc cac aac tgt atc cag aag gac agc aag gac tct ctc cac   1325
Leu Gln Val His Asn Cys Ile Gln Lys Asp Ser Lys Asp Ser Leu His
            300                 305                 310 gcc aac aca gcc aac cgc cgg acc acg ccc gta tga agaccgtggg        1371
Ala Asn Thr Ala Asn Arg Arg Thr Thr Pro Val
        315                 320 acgggggacc ctggggaggc ttggcccgcg ggcgggggag ggaccacagc agccacgggg  1431
agaccttcca tacgcaaaaa acaacaaaca agcaaacaag caaacgaaca aacaaacaac  1491
aaacaaacaa aacaaaaaac aaaacaaaaa aagagaaaa acatagcaag taaattaaaa   1551
aaaaaaa                                                            1558

<210> SEQ ID NO 8
<211> LENGTH: 323
<212> TYPE: PRT
<213> ORGANISM: Murinae gen. sp.

<400> SEQUENCE: 8

Met Gly Leu Phe Asp Arg Gly Val Gln Met Leu Leu Thr Thr Val Gly
  1               5                  10                  15

Ala Phe Ala Ala Phe Ser Leu Met Thr Ile Ala Val Gly Thr Asp Tyr
                 20                  25                  30

Trp Leu Tyr Ser Arg Gly Val Cys Lys Thr Lys Ser Val Ser Glu Asn
             35                  40                  45

Glu Thr Ser Lys Lys Asn Glu Glu Val Met Thr His Ser Gly Leu Trp
         50                  55                  60

Arg Thr Cys Cys Leu Glu Gly Asn Phe Lys Gly Leu Cys Lys Gln Ile
 65                  70                  75                  80

Asp His Phe Pro Glu Asp Ala Asp Tyr Glu Ala Asp Thr Ala Glu Tyr
                 85                  90                  95

Phe Leu Arg Ala Val Arg Ala Ser Ser Ile Phe Pro Ile Leu Ser Val
            100                 105                 110

Ile Leu Leu Phe Met Gly Gly Leu Cys Ile Ala Ala Ser Glu Phe Tyr
        115                 120                 125

Lys Thr Arg His Asn Ile Ile Leu Ser Ala Gly Ile Phe Phe Val Ser
    130                 135                 140

Ala Gly Leu Ser Asn Ile Ile Gly Ile Ile Val Tyr Ile Ser Ala Asn
145                 150                 155                 160

Ala Gly Asp Pro Ser Lys Ser Asp Ser Lys Lys Asn Ser Tyr Ser Tyr
                165                 170                 175

Gly Trp Ser Phe Tyr Phe Gly Ala Leu Ser Phe Ile Ile Ala Glu Met
            180                 185                 190

Val Gly Val Leu Ala Val His Met Phe Ile Asp Arg His Lys Gln Leu
        195                 200                 205

Arg Ala Thr Ala Arg Ala Thr Asp Tyr Leu Gln Ala Ser Ala Ile Thr
    210                 215                 220

Arg Ile Pro Ser Tyr Arg Tyr Arg Tyr Gln Arg Arg Ser Arg Ser Ser
```

-continued

| | | | | | | | | | | | | | | | |
|---|---|---|---|---|---|---|---|---|---|---|---|---|---|---|---|
|225| | | | |230| | | | |235| | | | |240|
|Ser|Arg|Ser|Thr|Glu|Pro|Ser|His|Ser|Arg|Asp|Ala|Ser|Pro|Val|Gly|
| | | | |245| | | | |250| | | | |255| |

Val Lys Gly Phe Asn Thr Leu Pro Ser Thr Glu Ile Ser Met Tyr Thr
            260                 265                 270

Leu Ser Arg Asp Pro Leu Lys Ala Ala Thr Thr Pro Thr Ala Thr Tyr
        275                 280                 285

Asn Ser Asp Arg Asp Asn Ser Phe Leu Gln Val His Asn Cys Ile Gln
    290                 295                 300

Lys Asp Ser Lys Asp Ser Leu His Ala Asn Thr Ala Asn Arg Arg Thr
305                 310                 315                 320

Thr Pro Val

<210> SEQ ID NO 9
<211> LENGTH: 1477
<212> TYPE: DNA
<213> ORGANISM: Murinae gen. sp.
<220> FEATURE:
<221> NAME/KEY: 5'UTR
<222> LOCATION: (1)..(487)
<220> FEATURE:
<221> NAME/KEY: CDS
<222> LOCATION: (488)..(1432)
<220> FEATURE:
<221> NAME/KEY: 3'UTR
<222> LOCATION: (1433)..(1477)

<400> SEQUENCE: 9
actcactata gggctcgagc ggccgcccgg gcaggtcacg cgcgcacaca cgcacacacg    60
ctcacacgct cacacaccag acctctctgg gtttcttttg ccttgagtct ctcggggctg   120
tgagaaacca ggcgcatctc aaaccaagct ggcggctcca agctccgaag ccatgccctg   180
cacaaacgct agtcctcacc aagctcctga ggaatgaaag caaccagga atcctctgac    240 cgcggcagtg atgtggacca accccctgga gcccgcaccc tcccgagggc catagaggac   300
tcggggaact ggagagagcc caagacagga atcccagct ttcccaaagt ccccgtggat    360
gctgacaaaa ggagatctgg attttggaa gaggccgtcc taggttaccc agctgcagag   420
tgattctccc gtctgtcact gaatctaccc ctccaacccc cagccgttca gagtaccatg   480 aagaatt atg agg atg tgt gac aga ggt atc cag atg ttg atc act act    529
        Met Arg Met Cys Asp Arg Gly Ile Gln Met Leu Ile Thr Thr
          1               5                  10 gta gga gcc ttc gca gct ttt agt tta atg acc att gca gtg ggc acg    577
Val Gly Ala Phe Ala Ala Phe Ser Leu Met Thr Ile Ala Val Gly Thr
 15              20                  25                  30 gac tac tgg cta tat tcc aga ggt gtg tgc agg act aaa tct aca agt    625
Asp Tyr Trp Leu Tyr Ser Arg Gly Val Cys Arg Thr Lys Ser Thr Ser
                 35                  40                  45 gac aat gaa acc agc agg aag aat gaa gaa gta atg acc cac tcc ggg    673
Asp Asn Glu Thr Ser Arg Lys Asn Glu Glu Val Met Thr His Ser Gly
             50                  55                  60 ttg tgg agg acc tgc tgc ttg gaa gga gct ttc cga ggc gtg tgc aag    721
Leu Trp Arg Thr Cys Cys Leu Glu Gly Ala Phe Arg Gly Val Cys Lys
         65                  70                  75 aaa atc gat cac ttc cca gaa gat gca gac tat gaa cag gat aca gca    769
Lys Ile Asp His Phe Pro Glu Asp Ala Asp Tyr Glu Gln Asp Thr Ala
     80                  85                  90 gaa tat ctt cta cga gct gtg agg gcc tcc agc gtc ttt ccc atc ctc    817
Glu Tyr Leu Leu Arg Ala Val Arg Ala Ser Ser Val Phe Pro Ile Leu
 95                 100                 105                 110

-continued

```
agc gtc act ctg ctg ttt ttc ggg gga ctc tgc gtg gct gcc agc gag        865
Ser Val Thr Leu Leu Phe Phe Gly Gly Leu Cys Val Ala Ala Ser Glu
            115                 120                 125 ttc cac cgc agc agg cac agt gtg atc ctc agc gct ggc atc ttc ttc        913
Phe His Arg Ser Arg His Ser Val Ile Leu Ser Ala Gly Ile Phe Phe
            130                 135                 140 gtc tct gca ggg cta agc aac atc atc ggc atc ata gtt tat atc tca        961
Val Ser Ala Gly Leu Ser Asn Ile Ile Gly Ile Ile Val Tyr Ile Ser
            145                 150                 155 gcc aat gct gga ggc cct ggg cag agg gac tct aaa aag agc tac tcc       1009
Ala Asn Ala Gly Gly Pro Gly Gln Arg Asp Ser Lys Lys Ser Tyr Ser
            160                 165                 170 tac ggc tgg tcc ttt tat ttt gga gcc ttc tct ttc atc atc gcg gaa       1057
Tyr Gly Trp Ser Phe Tyr Phe Gly Ala Phe Ser Phe Ile Ile Ala Glu
175                 180                 185                 190 att gtg ggc gtg gtc gcc gtg cac atc tat atc gag aag cat cag cag       1105
Ile Val Gly Val Val Ala Val His Ile Tyr Ile Glu Lys His Gln Gln
                195                 200                 205 ttg cgt gcc aga tcc cat tca gag ctc ctg aag aag tct aca ttt gcg       1153
Leu Arg Ala Arg Ser His Ser Glu Leu Leu Lys Lys Ser Thr Phe Ala
                210                 215                 220 cgc ctg ccg ccc tac agg tat aga ttc cga aga cgg tca agt tct cgc       1201
Arg Leu Pro Pro Tyr Arg Tyr Arg Phe Arg Arg Arg Ser Ser Ser Arg
            225                 230                 235 tcc act gaa ccc aga tct cga gac ctt tct ccc atc agc aaa ggc ttc       1249
Ser Thr Glu Pro Arg Ser Arg Asp Leu Ser Pro Ile Ser Lys Gly Phe
            240                 245                 250 cac acc atc cct tcc acc gac atc tcc atg ttc acc ctc tcc cgg gac       1297
His Thr Ile Pro Ser Thr Asp Ile Ser Met Phe Thr Leu Ser Arg Asp
255                 260                 265                 270 ccc tct aag ctt acc atg ggg acc ctt ctc aac tct gac cgg gac cat       1345
Pro Ser Lys Leu Thr Met Gly Thr Leu Leu Asn Ser Asp Arg Asp His
                275                 280                 285 gct ttt cta cag ttc cac aac tcc aca ccc aaa gag ttc aaa gag tca       1393
Ala Phe Leu Gln Phe His Asn Ser Thr Pro Lys Glu Phe Lys Glu Ser
            290                 295                 300 ttg cat aac aat ccg gcc aac aga cgt acc acg cct gtc tgagctgacc       1442
Leu His Asn Asn Pro Ala Asn Arg Arg Thr Thr Pro Val
            305                 310                 315 tctgacctct gccccgccgc ccagcacagc cttgg                                1477
```

<210> SEQ ID NO 10
<211> LENGTH: 315
<212> TYPE: PRT
<213> ORGANISM: Murinae gen. sp.

<400> SEQUENCE: 10

```
Met Arg Met Cys Asp Arg Gly Ile Gln Met Leu Ile Thr Thr Val Gly
  1               5                  10                  15

Ala Phe Ala Ala Phe Ser Leu Met Thr Ile Ala Val Gly Thr Asp Tyr
                 20                  25                  30

Trp Leu Tyr Ser Arg Gly Val Cys Arg Thr Lys Ser Thr Ser Asp Asn
             35                  40                  45

Glu Thr Ser Arg Lys Asn Glu Glu Val Met Thr His Ser Gly Leu Trp
         50                  55                  60

Arg Thr Cys Cys Leu Glu Gly Ala Phe Arg Gly Val Cys Lys Lys Ile
 65                  70                  75                  80

Asp His Phe Pro Glu Asp Ala Asp Tyr Glu Gln Asp Thr Ala Glu Tyr
```

```
                        85                  90                  95
Leu Leu Arg Ala Val Arg Ala Ser Ser Val Phe Pro Ile Leu Ser Val
                100                 105                 110

Thr Leu Leu Phe Phe Gly Gly Leu Cys Val Ala Ala Ser Glu Phe His
            115                 120                 125

Arg Ser Arg His Ser Val Ile Leu Ser Ala Gly Ile Phe Phe Val Ser
        130                 135                 140

Ala Gly Leu Ser Asn Ile Ile Gly Ile Ile Val Tyr Ile Ser Ala Asn
145                 150                 155                 160

Ala Gly Gly Pro Gly Gln Arg Asp Ser Lys Ser Tyr Ser Tyr Gly
                165                 170                 175

Trp Ser Phe Tyr Phe Gly Ala Phe Ser Phe Ile Ile Ala Glu Ile Val
            180                 185                 190

Gly Val Val Ala Val His Ile Tyr Ile Glu Lys His Gln Gln Leu Arg
            195                 200                 205

Ala Arg Ser His Ser Glu Leu Leu Lys Lys Ser Thr Phe Ala Arg Leu
        210                 215                 220

Pro Pro Tyr Arg Tyr Arg Phe Arg Arg Ser Ser Ser Arg Ser Thr
225                 230                 235                 240

Glu Pro Arg Ser Arg Asp Leu Ser Pro Ile Ser Lys Gly Phe His Thr
                245                 250                 255

Ile Pro Ser Thr Asp Ile Ser Met Phe Thr Leu Ser Arg Asp Pro Ser
            260                 265                 270

Lys Leu Thr Met Gly Thr Leu Leu Asn Ser Asp Arg Asp His Ala Phe
        275                 280                 285

Leu Gln Phe His Asn Ser Thr Pro Lys Glu Phe Lys Glu Ser Leu His
    290                 295                 300

Asn Asn Pro Ala Asn Arg Arg Thr Thr Pro Val
305                 310                 315

<210> SEQ ID NO 11
<211> LENGTH: 1071
<212> TYPE: DNA
<213> ORGANISM: Murinae gen. sp.
<220> FEATURE:
<221> NAME/KEY: 5'UTR
<222> LOCATION: (1)..(21)
<220> FEATURE:
<221> NAME/KEY: CDS
<222> LOCATION: (22)..(1002)
<220> FEATURE:
<220> FEATURE:
<221> NAME/KEY: 3'UTR
<222> LOCATION: (1003)..(1071)

<400> SEQUENCE: 11
gcggactatg aggcgcccac c atg gtg cga tgc gac cgc ggg ctg cag atg       51
                        Met Val Arg Cys Asp Arg Gly Leu Gln Met
                         1               5                  10 ctg ctg acc acg gcc gga gcc ctc gcc gcc ttc tcg ctc atg gcc atc     99
Leu Leu Thr Thr Ala Gly Ala Leu Ala Ala Phe Ser Leu Met Ala Ile
             15                  20                  25 gcc atc ggc acc gac tac cgg ctg tac tcc agc gcg cac atc tgc aac    147
Ala Ile Gly Thr Asp Tyr Arg Leu Tyr Ser Ser Ala His Ile Cys Asn
         30                  35                  40 ggc acc aac ctg acc atg gac gac ggg ccc ccg ccc cgc cgc gct cgc    195
Gly Thr Asn Leu Thr Met Asp Asp Gly Pro Pro Pro Arg Arg Ala Arg
     45                  50                  55 ggc gac ctc acc cat tcg gga ctg tgg cgg gtg tgt tgc atc gaa ggc    243
```

```
            Gly Asp Leu Thr His Ser Gly Leu Trp Arg Val Cys Cys Ile Glu Gly
                 60                  65                  70 atc tat aga ggg cac tgc ttc cgg atc aac cac ttc cca gag gac aac        291
Ile Tyr Arg Gly His Cys Phe Arg Ile Asn His Phe Pro Glu Asp Asn
 75                  80                  85                  90 gat tac gac cac gac agc tcc gag tac ctc ctc cgc att gtg cga gcc        339
Asp Tyr Asp His Asp Ser Ser Glu Tyr Leu Leu Arg Ile Val Arg Ala
                 95                 100                 105 tcc agt gtc ttt ccc atc ctc agc acc att ctg ctc ctg ctc gga ggg        387
Ser Ser Val Phe Pro Ile Leu Ser Thr Ile Leu Leu Leu Leu Gly Gly
                110                 115                 120 ctc tgc atc ggc gct ggg agg atc tac agc cgc aac aac aat att gtc        435
Leu Cys Ile Gly Ala Gly Arg Ile Tyr Ser Arg Asn Asn Asn Ile Val
                125                 130                 135 ctc agc gcg gga atc ctc ttt gtg gcg gca ggc ctc agt aat atc atc        483
Leu Ser Ala Gly Ile Leu Phe Val Ala Ala Gly Leu Ser Asn Ile Ile
140                 145                 150 ggt atc atc gtc tac att tcc agc aac acg ggc gac ccc agt gac aaa        531
Gly Ile Ile Val Tyr Ile Ser Ser Asn Thr Gly Asp Pro Ser Asp Lys
155                 160                 165                 170 cgt gac gaa gac aaa aag aac cat tac aac tac ggc tgg tct ttt tac        579
Arg Asp Glu Asp Lys Lys Asn His Tyr Asn Tyr Gly Trp Ser Phe Tyr
                175                 180                 185 ttt gga gcc ctg tcg ttt att gtg gcg gag acc gtg ggc gtc ctg gct        627
Phe Gly Ala Leu Ser Phe Ile Val Ala Glu Thr Val Gly Val Leu Ala
                190                 195                 200 gta aac att tac att gag aaa aat aaa gag ttg agg ttt aag acc aag        675
Val Asn Ile Tyr Ile Glu Lys Asn Lys Glu Leu Arg Phe Lys Thr Lys
                205                 210                 215 cgg gag ttc ctt aag gcc tct tcc tcc tct cct tac gcc agg atg ccg        723
Arg Glu Phe Leu Lys Ala Ser Ser Ser Ser Pro Tyr Ala Arg Met Pro
220                 225                 230 agc tac agg tac cgg cga cgg cgg tcc agg tcc agt tca agg tcc acg        771
Ser Tyr Arg Tyr Arg Arg Arg Arg Ser Arg Ser Ser Arg Ser Thr
235                 240                 245                 250 gag gcc tca ccc tcc agg gat gca tct ccc gtg ggc ctg aag atc acc        819
Glu Ala Ser Pro Ser Arg Asp Ala Ser Pro Val Gly Leu Lys Ile Thr
                255                 260                 265 gga gcc att ccc atg ggt gag ctg tcc atg tac acg cta tcc aga gaa        867
Gly Ala Ile Pro Met Gly Glu Leu Ser Met Tyr Thr Leu Ser Arg Glu
                270                 275                 280 ccc ctt aag gtg acc aca gct gcg agc tac agt ccg gac cag gac gct        915
Pro Leu Lys Val Thr Thr Ala Ala Ser Tyr Ser Pro Asp Gln Asp Ala
                285                 290                 295 ggc ttc ctg cag atg cat gac ttc ttc caa cag gac cta aag gaa ggt        963
Gly Phe Leu Gln Met His Asp Phe Phe Gln Gln Asp Leu Lys Glu Gly
300                 305                 310 ttc cat gtc agc atg ctk aac cgg cgg acr act ccc gtg tgacccgccc       1012
Phe His Val Ser Met Xaa Asn Arg Arg Xaa Thr Pro Val
315                 320                 325 acccctctcg gcacaggcct cccccaaggt ggctgtttgt gtgacacaga acagggtga    1071

<210> SEQ ID NO 12
<211> LENGTH: 327
<212> TYPE: PRT
<213> ORGANISM: Murinae gen. sp.

<400> SEQUENCE: 12

Met Val Arg Cys Asp Arg Gly Leu Gln Met Leu Leu Thr Thr Ala Gly
 1               5                  10                  15
```

```
Ala Leu Ala Ala Phe Ser Leu Met Ala Ile Ala Ile Gly Thr Asp Tyr
             20                  25                  30
Arg Leu Tyr Ser Ser Ala His Ile Cys Asn Gly Thr Asn Leu Thr Met
         35                  40                  45
Asp Asp Gly Pro Pro Arg Ala Arg Gly Asp Leu Thr His Ser
     50                  55                  60
Gly Leu Trp Arg Val Cys Cys Ile Glu Gly Ile Tyr Arg Gly His Cys
 65                  70                  75                  80
Phe Arg Ile Asn His Phe Pro Glu Asp Asn Asp Tyr Asp His Asp Ser
                 85                  90                  95
Ser Glu Tyr Leu Leu Arg Ile Val Arg Ala Ser Ser Val Phe Pro Ile
            100                 105                 110
Leu Ser Thr Ile Leu Leu Leu Gly Gly Leu Cys Ile Gly Ala Gly
            115                 120                 125
Arg Ile Tyr Ser Arg Asn Asn Asn Ile Val Leu Ser Ala Gly Ile Leu
            130                 135                 140
Phe Val Ala Ala Gly Leu Ser Asn Ile Ile Gly Ile Ile Val Tyr Ile
145                 150                 155                 160
Ser Ser Asn Thr Gly Asp Pro Ser Asp Lys Arg Asp Glu Asp Lys Lys
                165                 170                 175
Asn His Tyr Asn Tyr Gly Trp Ser Phe Tyr Phe Gly Ala Leu Ser Phe
            180                 185                 190
Ile Val Ala Glu Thr Val Gly Val Leu Ala Val Asn Ile Tyr Ile Glu
            195                 200                 205
Lys Asn Lys Glu Leu Arg Phe Lys Thr Lys Arg Glu Phe Leu Lys Ala
210                 215                 220
Ser Ser Ser Pro Tyr Ala Arg Met Pro Ser Tyr Arg Tyr Arg Arg
225                 230                 235                 240
Arg Arg Ser Arg Ser Ser Arg Ser Thr Glu Ala Ser Pro Ser Arg
                245                 250                 255
Asp Ala Ser Pro Val Gly Leu Lys Ile Thr Gly Ala Ile Pro Met Gly
            260                 265                 270
Glu Leu Ser Met Tyr Thr Leu Ser Arg Glu Pro Leu Lys Val Thr Thr
            275                 280                 285
Ala Ala Ser Tyr Ser Pro Asp Gln Asp Ala Gly Phe Leu Gln Met His
    290                 295                 300
Asp Phe Phe Gln Gln Asp Leu Lys Glu Gly Phe His Val Ser Met Xaa
305                 310                 315                 320
Asn Arg Arg Xaa Thr Pro Val
            325
```

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 13
ctcaaaagct tgatgaccat c                                          21

<210> SEQ ID NO 14
<211> LENGTH: 21
<212> TYPE: DNA
<213> ORGANISM: Artificial Sequence
<220> FEATURE:

<223> OTHER INFORMATION: Description of Artificial Sequence: primer

<400> SEQUENCE: 14
accatctcgg cgatgatgaa g                                21

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 15
acgaagaagg tgccagca                                    18

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 16
tgcggtgtca gcttcgtagt c                                21

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 17
aagttccctt cgaggcag                                    18

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 18
catttcctgt ctcatccttt g                                21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 19
gccttgatca gagtaactgt c                                21

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 20
gagcaagcag gtttcaggc                                   19

-continued

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 21
actgtcactc tatctggaat c                                          21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 22
gcggttattg ttcttggcgg c                                          21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 23
ggaactgtgg aacaggagtc c                                          21

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 24
tctggagtac agccaata                                              18

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 25
tggaattacc aatcgcacc                                             19

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 26
tacggctggt ccttctactt c                                          21

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: primer

```
<400> SEQUENCE: 27
tagtaatatc atcgggat                                              18

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 28
ccacggggaa gaccttccat a                                          21

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 29
cacgccaccc accggagaat g                                          21

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 30
gatgctgatc acatgtctcg                                            20

<210> SEQ ID NO 31
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 31
tctgaattcg cctccgccat cacccgcatc cccagctac                       39

<210> SEQ ID NO 32
<211> LENGTH: 41
<212> TYPE: DNA
<213> ORGANISM: Artificial Sequence
<220> FEATURE:
<223> OTHER INFORMATION: Description of Artificial Sequence: primer

<400> SEQUENCE: 32
tatttcgtcg actcttcata ctggcgtggt ccggcggttg g                    41

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 33
tgtggaggac ctgctgccta gaag                                       24

<210> SEQ ID NO 34
<211> LENGTH: 24
```

```
<212> TYPE: DNA
<213> ORGANISM: Artificial Sequence
<220> FEATURE:
<223> OTHER INFORMATION: Description of Artificial Sequence: primer

<400> SEQUENCE: 34
accatcacaa ggaccatgcc atgc                                           24

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 35
cagagacatc tctgtacact tccc                                           24

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 36
gcaaaggctt ccacaccatc                                                20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 37
ggaaggacag agtcaaaggc                                                20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 38
aagaggcctt aaggaactcc                                                20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 39
ctgagctcag aatgtacagg                                                20

<210> SEQ ID NO 40
<211> LENGTH: 20
<212> TYPE: DNA
<213> ORGANISM: Artificial Sequence
```

-continued

```
<220> FEATURE:
<223> OTHER INFORMATION: Description of Artificial Sequence: primer

<400> SEQUENCE: 40
atctgtgtca gaacaccagg                                              20
```